US006455515B2

United States Patent
Gypser et al.

(10) Patent No.: US 6,455,515 B2
(45) Date of Patent: Sep. 24, 2002

(54) SALICYLOHYDRAZIDE DERIVATIVES, PROCESSES AND INTERMEDIATES FOR THEIR PREPARATION, COMPOSITIONS COMPRISING THEM, AND THEIR USE

(75) Inventors: Andreas Gypser, Mannheim; Thomas Grote, Wachenheim; Joachim Rheinheimer, Ludwigshafen; Ingo Rose, Mannheim; Peter Schäfer, Ottersheim; Oliver Cullmann, Heppenheim; Markus Gewehr, Kastellaun; Wassilios Grammenos, Ludwigshafen; Jordi Tormo i Blasco, Limburgerhof; Bernd Müller, Frankenthal; Hubert Sauter, Mannheim; Eberhard Ammermann, Heppenheim; Siegfried Strathmann, Limburgerhof; Gisela Lorenz, Hambach; Reinhard Stierl, Mutterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/879,902

(22) Filed: Jun. 14, 2001

(30) Foreign Application Priority Data

Jun. 16, 2000 (DE) .......................................... 100 28 978

(51) Int. Cl.$^7$ ........................ A01N 37/40; C07C 235/44
(52) U.S. Cl. ...................... 514/166; 564/148; 564/150; 514/159
(58) Field of Search ................ 564/148, 150; 514/166

(56) References Cited

U.S. PATENT DOCUMENTS

| | | | |
|---|---|---|---|
| 3,424,845 A | 1/1969 | Berndt et al. ................ 424/232 |
| 3,773,943 A | * 11/1973 | Welch et al. ................ 514/472 |
| 3,829,492 A | 8/1974 | Miller et al. ................. 260/566 |
| 5,254,717 A | 10/1993 | Grammenos et al. .......... 560/35 |
| 6,001,879 A | 12/1999 | Seitz et al. .................. 514/616 |

FOREIGN PATENT DOCUMENTS

| DE | 197 10 609 | 9/1998 |
|---|---|---|
| WO | WO 97/08135 | 3/1997 |
| WO | WO 99/27783 | 6/1999 |

OTHER PUBLICATIONS

Kazadova et al., Chemical Abstracts, 120:243954 (1994).*
Piscopo et al., Chemical Abstracts, 99:19571 (1983).*
Plessing et al., Chemical Abstracts, 57:2853 (1962).*
Sullivan et al., Chemical Abstracts, 78:143662 (1973).*
Welch et al., Chemical Abstracts, 72:100393 (1970).*
Berdinski et al., Chemical Abstracts 64:12595 (1966).*
Feuer et al., Chemical Abstracts, 63:11411 (1965).*
Prakash et al., Chemical Abstracts, 62:11804 (1965).*
Daeniker, Chemical Abstracts, 60:10592 (1964).*
Cioranescu et al., Chemical Abstracts, 58:6741 (1963).*
Maskar et al. Chemical Abstract No. 60, No. 10592 (1964).
Berndt et al. "3,5–Dinitrosalicylic Acid (5–Nitrofurfurylidene) hydriazide, a Potent New Preventive of Histomoniasis in Turkeys" Journal of Medicinal Chemistry vol. 12 (1969) pp. 371–374.
Haksar et al. "Study of Some Benzohydrazides" Chemical Abstracts vol. 58, No. 67401 (1963).
Haksar et al. Chemical Abstract No. 64, No. 12595 (1966).
Devgan et al. Chemical Abstract No. 63, No. 11411 (1965).

* cited by examiner

Primary Examiner—Fiona T. Powers
(74) Attorney, Agent, or Firm—Keil & Weinkauf

(57) ABSTRACT

Salicylohydrazide derivatives of the formula I

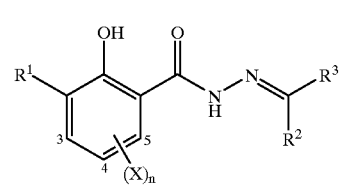

in which the index and the substituents have the following meanings:

X is halogen, $NO_2$, cyano, alkyl or alkoxy;
m is 0, 1, 2 or 3, it being possible for the substituents X to differ from each other if n is greater than 1;
$R^1$ is $NO_2$, $NH_2$ or NH—CO—A;
A is hydrogen, alkyl, alkoxy, $NH_2$, $NHCH_3$ or $N(CH_3)_2$;
$R^2$ is hydrogen, cyano, alkyl, alkenyl, alkynyl, haloalkyl, alkoxy or alkylthio;
  it being possible for the hydrocarbon radicals to be unsubstituted or substituted,
$R^3$ is phenyl, naphthyl, cycloalkyl, 5-membered or 6-membered hetaryl or 5-membered or 6-membered heterocyclyl containing one to three N atoms and/or one O or S atom or one or two O and/or S atoms, the ring systems being unsubstituted or substituted;
the preparation of these compounds, compositions comprising them, and their use for controlling harmful fungi.

6 Claims, No Drawings

SALICYLOHYDRAZIDE DERIVATIVES, PROCESSES AND INTERMEDIATES FOR THEIR PREPARATION, COMPOSITIONS COMPRISING THEM, AND THEIR USE

Salicylohydrazide derivatives, processes and intermediates for their preparation, compositions comprising them, and their use The present invention relates to salicylohydrazide derivatives of the formula I

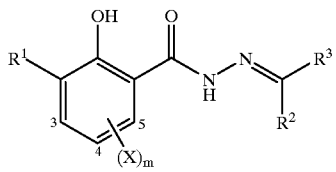

in which the index and the substituents have the following meanings:

X is halogen, $NO_2$, cyano, $C_1$–$C_4$-alkyl or $C_1$–$C_4$-alkoxy;
m is 0, 1, 2 or 3, it being possible for the substituents X to differ from each other if n is greater than 1;
$R^1$ is $NO_2$, $NH_2$ or NH—CO—A;
  A is hydrogen, $C_1$–$C_4$-alkyl, $C_1$–$C_4$-alkoxy, $NH_2$, $NHCH_3$ or $N(CH_3)_2$;
$R^2$ is hydrogen, cyano, $C_1$–$C_6$-alkyl, $C_2$–$C_6$-alkenyl, $C_2$–$C_6$-alkynyl, $C_1$–$C_6$-haloalkyl, $C_1$–$C_6$-alkoxy or $C_1$–$C_6$-alkylthio;
  it being possible for the hydrocarbon radicals to be unsubstituted or to be partially or fully halogenated or to have 1 to 3 groups $R^a$
    $R^a$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_3$–$C_6$-alkenyloxy, $C_3$–$C_6$-alkynyloxy or $C_1$–$C_4$-alkylenedioxy which can be halogenated,
$R^3$ is phenyl, naphthyl, $C_3$–$C_{10}$-cycloalkyl, 5-membered or 6-membered hetaryl or 5-membered or 6-membered heterocyclyl containing one to three N atoms and/or one O or S atom or one or two O and/or S atoms, the ring systems being unsubstituted or substituted by one to three radicals $R^b$:
  $R^b$ is cyano, nitro, amino, aminocarbonyl, aminothiocarbonyl, halogen, hydroxyl, $C_1$–$C^6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, phenyl, phenoxy, benzyl, benzyloxy, 5- or 6-membered heterocyclyl, 5- or 6-membered hetaryl, 5- or 6-membered hetaryloxy, C(=$NOR^α$)—$OR^β$ or $OC(R^α)_2$—C ($R^β$)=$NOR^β$,
    the cyclic radicals, in turn, being unsubstituted or substituted by one to three radicals $R^c$:
      $R^c$ is cyano, nitro, halogen, hydroxyl, amino, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl. $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or C(=$NOR^α$)—$OR^β$;
$R^α$, $R^β$ are hydrogen or $C_1$–$C_6$-alkyl.

Furthermore, the invention relates to processes for the preparation of these compounds, to compositions comprising them, and to their use for controlling harmful fungi.

WO-A 97/08135, DE-A 197 10 609 and WO-A 99/27783 disclose acylaminosalicylamides for controlling harmful fungi.

However, their action is unsatisfactory in many cases. Compounds with an improved action are an object of the present invention.

We have found that this object is achieved by the compounds defined at the outset. Moreover, there have been found processes for their preparation, compositions comprising them, and methods of controlling harmful fungi using the compounds I.

The compounds of the formula I differ from those known from the prior art by the hydrazide group.

Compared with the known compounds, the compounds of the formula I exhibit an increased efficacy against harmful fungi.

For example, compounds of the formula I can be synthesized starting from hydrazides of the formula II by subjecting hydrazides and carbonyl compounds of the formula III to a condensation reaction. The compounds of the formula IA are also used as intermediates for the preparation of further compounds I.

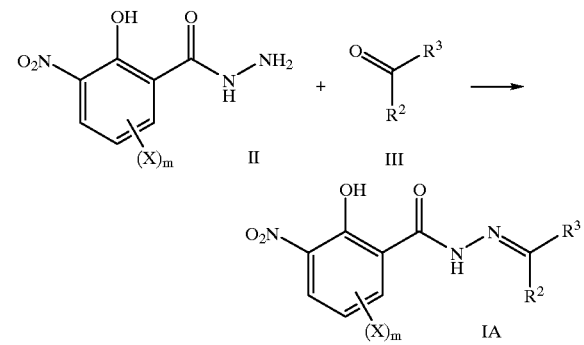

This reaction is usually carried out at temperatures from 20° C. to 100° C., preferably 20° C. to 50° C., in an inert organic solvent in the presence of an acid [cf. Indian J. Chem. B, (1983), Vol. 24, p. 979].

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methylether, dioxane and tetrahydrofuran, nitriles such as acetonitrile and propionitrile, alcohols such as methanol, ethanol, n-propanol, isopropanol and n-butanol, and also dimethyl sulfoxide, dimethylformamide and dimethylacetamide, especially preferably alcohols such as methanol, ethanol, n-propanol, isopropanol and n-butanol. Mixtures of these solvents may also be used.

Acid and acidic catalysts which are used are inorganic acids such as hydrofluoric acid, (aqueous) hydrochloric acid, tetrabromic acid, sulfuric acid and perchloric acid, Lewis acids such as boron trifluoride, aluminum trichloride, iron (III) chloride, tin(IV) chloride, titanium(IV) chloride and zinc(II) chloride, and organic acids such as formic acid, acetic acid, propionic acid, oxalic acid, citric acid, trifluoroacetic acid, p-toluenesulfonic acid, benzenesulfonic acid and camphorsulfonic acid.

In general, the acids are employed in catalytic amounts, but they may also be used in equimolar amounts, in an excess or, if appropriate, as solvent.

In general, the starting materials are reacted with each other in equimolar amounts. It may be advantageous for the yield to employ III in an excess based on II.

The starting materials II and III required for the preparation of compounds I are commercially available, known from the literature [ZA 70/00662; Labdev, (1973), part A, Vol. 11A(1–2), p. 35] or can be prepared in accordance with the literature cited.

To prepare compounds I where $R^1$ is $NH_2$ or NH—CO—A, hydrazides of the formula IA are reduced to aminophenol compounds of the formula IB.

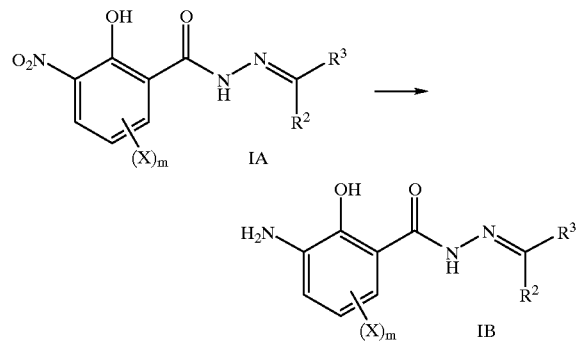

The nitro group of IA can be reduced under generally customary conditions by reduction with iron, tin or zinc in the presence of an acid or by enzyme-catalyzed reduction [cf. Houben-Weyl, Vol. IV/1c, 4th Ed., p. 506, Thieme Verlag Stuttgart and New York (1980); ibid. Vol. IV/1d, 4th Ed., p. 473 (1981); Heterocycles (1990), Vol. 31. p. 2201].

The reaction with hydrogen is preferably carried out by catalytic hydrogenation at −20° C. and +180° C., preferably between −5 and +40° C. The minimum temperature is only determined by the freezing point of the solvent used. Normally, the hydrogenation is carried out at a hydrogen pressure between atmospheric pressure and at an superatmospheric pressure of 30 bar. Normally, the hydrogen is passed in under atmospheric or slight superatmospheric pressure [cf. WO-A 97/08135].

Catalysts which are employed for the catalytic hydrogenation are commercially available catalysts which comprise, for example, platinum, platinum oxide or palladium on a support, or else Raney nickel or Raney cobalt.

The use of platinum catalysts or palladium catalysts is preferred. The platinum or palladium content of the catalyst is not critical and can be varied within wide limits. A content of from 0.1 to 15% by weight, preferably from 0.5 to 10% by weight, based on the support material, is expedient. The amount of the platinum or palladium employed is between 0.001 and 10% by weight, preferably between 0.01 and 0.1% by weight, based on the nitro compound. In the preferred embodiment, carbon is used as support material. Other non-amphoteric supports such as graphite, $BaSO_4$ or SiC, are also suitable.

Suitable diluents are esters such as ethyl acetate, alcohols such as methanol, ethanol, n-propanol, n-, i-, sec- or tert-butanol, ethanediol, propane-1,2-diol, ethoxyethanol, methoxyethanol, ethers such as diethylene glycol monomethyl ether, diethylene glycol monomethyl ether, water, aqueous salt solutions such as, for example, ammonium chloride solution, acids, such as, for example, hydrochloric acid or acetic acid; methanol, ethanol and water are especially preferred. Mixtures of these diluents may also be used.

In general, the acids are employed in catalytic amounts, but they may also be used in equimolar amounts, in an excess or, if appropriate, as solvent.

To prepare compounds I in which $R^1$ is NH—CO—A, aminophenols of the formula IB are used as intermediates.

The aminophenols of the formula IB are preferably formylated with formic acid. This gives directly the compounds of the formula I in which $R^1$ is NH—CO—H, which correspond to the formula I.1.

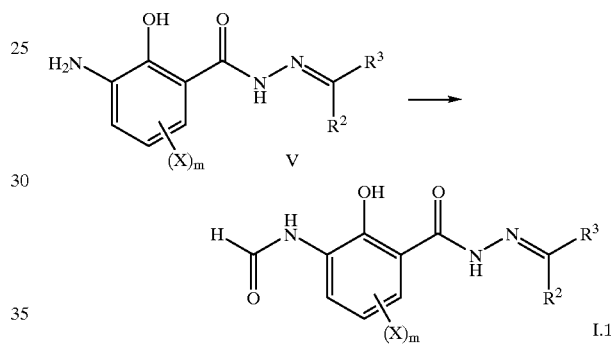

This reaction is usually carried out at temperatures of from 20° C. to 100° C., preferably from 20° C. to 80° C., in an inert organic solvent in the presence of an acid.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran. Mixtures of the solvents stated may also be used.

Acids and acidic catalysts which are used are inorganic acids such as hydrofluoric acid, aqueous hydrochloric acid, hydrobromic acid, sulfuric acid and perchloric acid, Lewis acids such as boron trifluoride, aluminum trichloride, iron (III) chloride, tin(IV) chloride, titanium(IV) chloride and zinc(II) chloride, and organic acids such as formic acid, acetic acid, propionic acid, oxalic acid, citric acid, trifluoroacetic acid, p-toluenesulfonic acid, benzenesulfonic acid and camphorsulfonic acid.

In general, the acids are employed in catalytic amounts, but they may also be used in equimolar amounts, in an excess or, if appropriate, as solvent.

In general, the starting materials are reacted with each other in equimolar amounts. It may be advantageous for the yield to employ formic acid in an excess based on V.

The compounds of the formula IB can be used to obtain the compounds of the formula I in which $R^1$ is NH—CO—A, where A is $NH_2$, $NHCH_3$, $N(CH_3)_2$ or $OCH_3$.

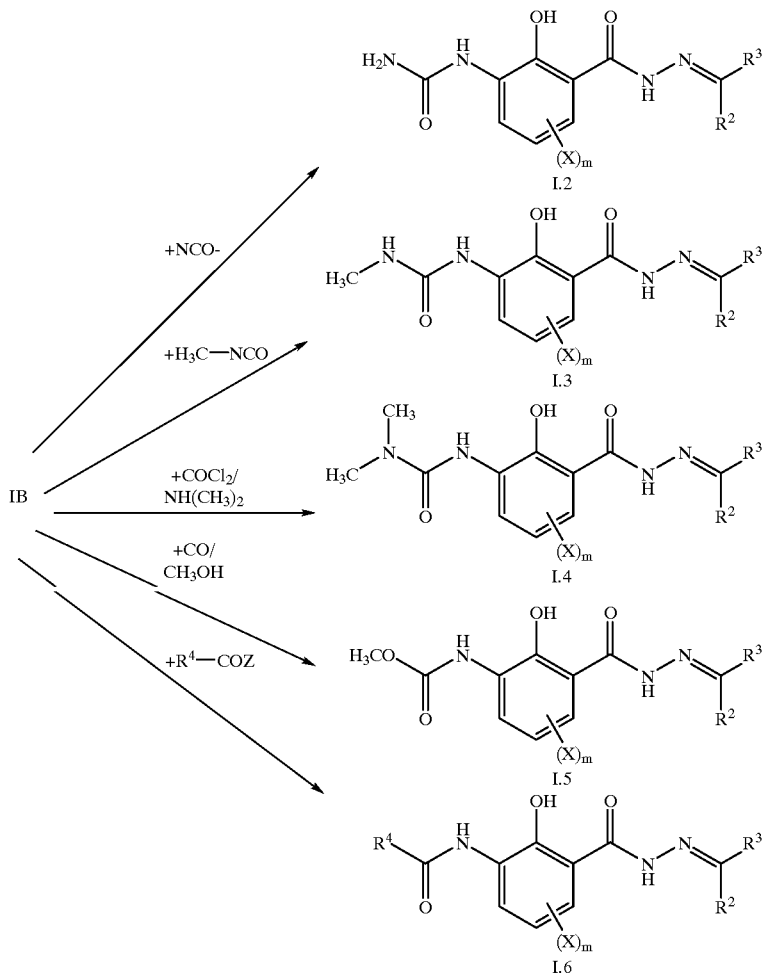

The compounds of the formula IB are derivatized to give the compounds of the formulae I.2 to I.6 by means of methods known from the following documents, whose disclosure is herewith incorporated: J. Med. Chem. (1989), Vol. 32, pp. 990–997; J. Org. Chem. (1961), Vol. 26, p. 5238; J. Chem. Res. Synop. (1998), 442; Tetrahedron Lett. (1994). Vol. 35, p. 8761.

The reaction of IB with alkali metal isocyanates or alkaline earth metal isocyanates, in particular sodium isocyanate, to give urea derivatives I.2 is carried out under the conditions known from J. Med. Chem. (1989), Vol. 32, pp. 990–997.

The reaction of IB with methyl isocyanate to give urea derivatives I.3 is carried out under the conditions known from J. Org. Chem. (1961), Vol. 26, p. 5238.

The reaction of IB with dimethylamine and phosgene or a phosgene equivalent such as di- or triphosgene to give urea derivatives I.4 is carried out under the conditions known from J. Chem. Res. Synop. (1998), 442. The use of di- or triphosgene is preferred for practical reasons.

The reaction of IB with carbon monoxide and methanol to give urea derivatives I.5 is carried out with transition metal catalysis under the conditions known from Tetrahedron Lett. (1994), Vol. 35, p. 8761.

Compounds of the formula I in which $R^1$ is NH—CO—A where A is $C_1$–$C_4$-alkyl can be obtained from the aminophenol compounds of the formula IB by acylation with alkyl-carboxylic acid derivatives of the formula IV in which $R^4$ is $C_1$–$C_4$-alkyl and Z is a nucleophilic leaving group such as alkoxy or halogen. The acylamino derivatives are described by the formula I.6 in which $R^4$ is $C_1$–$C_4$-alkyl.

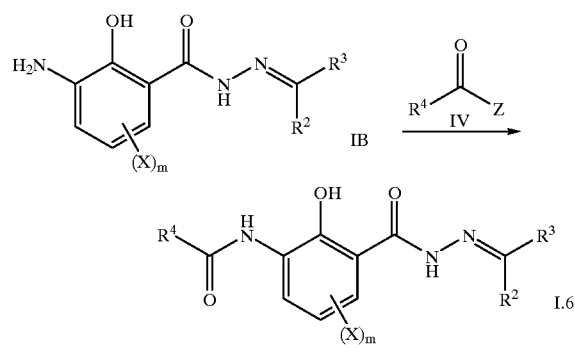

The acylation of V is carried out under conditions known per se from the literature, it is usually carried out at temperatures of from −20° C. to +80° C., preferably from 0° C. to +60° C., in an inert organic solvent in the presence of a base [cf. Organikum [Organic Chemistry], 15th Ed., p. 508 et seq., VEB Deutscher Verlag der Wissenschaften Berlin (1981)].

Suitable solvents are water, aliphatic hydrocarbons, aromatic hydrocarbons, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles, ketones, alcohols, and also dimethyl sulfoxide, dimethylformamide and dimethyl acetamide, especially preferably tetrahydrofuran and methylene chloride. Mixtures of the solvents stated may also be used.

Suitable bases are, in general, inorganic compounds such as alkali metal hydroxides and alkaline earth metal hydroxides, alkali metal oxides and alkaline earth metal oxides, alkali metal hydrides and alkaline earth metal hydrides, alkali metal carbonates and alkaline earth metal carbonates, alkali metal hydrogencarbonates and also alkali metal alkoxides and alkaline earth metal alkoxides, furthermore organic bases, for example tertiary amines such as trimethylamine, triethylamine, tri-isopropylethylamine and N-methylpiperidine, pyridine, substituted pyridines such as collidin, lutidin and 4-dimethylaminopyridine, and bicyclic amines. Pyridine and triethylamine are especially preferred. In general, the bases are employed in equimolar amounts, in an excess or, if appropriate, as a solvent.

In general, the starting materials are reacted with each other in equimolar amounts. It may be advantageous for the yield to employ the reactant(s) in an excess based on IB.

If individual compounds I are not accessible via the routes described above, they can be prepared by derivatizing other compounds I.

The reaction mixtures are worked up in the customary manner, for example by mixing with water, separating the phases and, if appropriate, purifying the crude products by chromatography. Some of the intermediates and end products are obtained in the form of colorless or pale brown, viscous oils, which are purified or freed from volatile components under reduced pressure and at moderately elevated temperature. If the intermediates and end products are obtained as solids, they may also be purified by recrystallization or digestion.

In the definitions of the symbols in the above formulae, collective terms were used which generally represent the following substituents:

halogen: fluorine, chlorine, bromine and iodine;

alkyl: saturated, straight-chain or branched hydrocarbon radicals having 1 to 4, 6, 8 or 10 carbon atoms, for example $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

halogenalkyl: straight-chain or branched alkyl groups having 1 to 10 carbon atoms (as mentioned above), it being possible for some or all of the hydrogen atoms in these groups to be replaced by halogen atoms as mentioned above, for example $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 6 carbon atoms (as mentioned above) which are bonded to the skeleton via an oxygen atom (—O—);

alkenyl: unsaturated, straight-chain or branched hydrocarbon radicals having 2 to 4 or 6 carbon atoms and one double bond in any position, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-7-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 4 or 6 carbon atoms and one triple bond in any position, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic saturated hydrocarbon groups saving 3 to 6 carbon ring members such as cyclopropyl, cyclobutyl, cyclopentyl and cyclohexyl;

5- or 6-membered heterocyclyl contains, in addition to carbon ring members, one to three nitrogen atoms and/or one oxygen or sulfur atom or one or two oxygen and/or sulfur atoms, e.g. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

5-membered heteroaryl contains one to four nitrogen atoms or one to three nitrogen atoms and one sulfur or oxygen atom: 5-membered cyclic heteroaryl groups which, besides carbon atoms, may contain one to four nitrogen atoms or one to three nitrogen atoms and one sulfur or oxygen atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl contains one to three or one to four nitrogen atoms: 6-membered cyclic heteroaryl groups which, besides carbon atoms, may contain one to three or one to four nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

alkylene: divalent unbranched chains made up by 1 to 4 $CH_2$ groups, e.g. $CH_2$, $CH_2CH_2$, $CH_2CH_2CH_2$ and $CH_2CH_2CH_2CH_2$;

alkylenedioxy: divalent unbranched chains made up of 1 to 3 $CH_2$ groups, both valencies being bound to the skeleton via an oxygen atom, e.g. $OCH_2O$, $OCH_2CH_2O$ and $OCH_2CH_2CH_2O$.

With regard of the intended use of the salicylohydrazide derivatives of the formula I, the following meanings of the substituents are especially preferred, in each case alone or in combination:

Especially preferred are compounds of the formula IA.

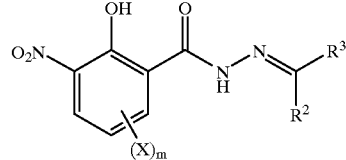

IA

Especially preferred are compounds of the formula I where $R^1$ is NH—CO—A; these compounds are described with the formula IC:

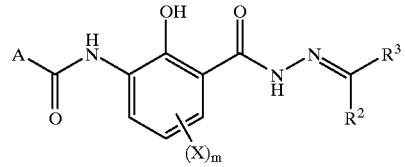

IC

Also especially preferred are compounds I.1.

Equally, other preferred compounds are those of the formula I.6 where $R^4$ is methyl; these compounds are described by the formula I.6a:

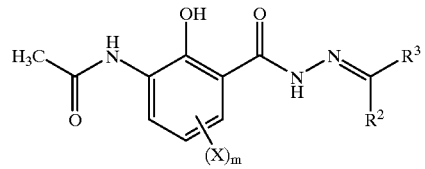

I.6a

Besides, especially preferred compounds I are those where the index m is zero; these compounds are described by the formula ID:

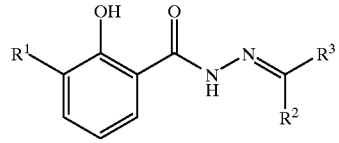

ID

In addition, especially preferred compounds I are those where $(X)_m$ is in the para-position relative to the phenol-OH group and is halogen, $NO_2$, CN and $C_1$–$C_4$-alkoxy, in particular 4-chloro, 4-bromo and 4-$NO_2$.

Equally especially preferred are compounds I where $R^2$ is hydrogen, methyl, ethyl, n-propyl, isopropyl and cyano, in particular hydrogen and methyl.

Other particularly preferred compounds I are those where $R^3$ is cyclohexyl and phenyl, each of which is optionally substituted by one to three radicals $R^b$, in particular phenyl. In the case of compounds in which $R^3$ is cyclohexyl, the substituent $R^b$ can be in the E- or Z-position relative to the C—$R^3$ bond.

In addition, especially preferred compounds I are those where $R^3$ is pyrazolyl, pyrimidinyl, pyridinyl, pyrazinyl and thiophenyl, each of which is optionally substituted by one to three radicals $R^b$.

The especially preferred use forms of the intermediates with regard to the variables correspond to those of the radicals $(X)_m$, $R^1$, A, $R^2$ and $R^3$ of the formula I.

Especially preferred with regard to their use are the compounds I which are compiled in the following tables. In the tables, the groups mentioned for a substituent additionally represent an especially preferred embodiment of the substituent in question in their own right, independently of the combination in which they are mentioned.

Table 1
Compounds of the formula IA where m is zero, $R^2$ is hydrogen and the radical $R^3$ for each compound corresponds to one line of Table A

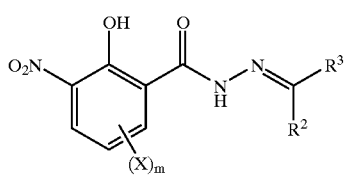

IA

Table 2
Compounds of the formula IA where m is zero, $R^2$ is methyl and the radical $R^3$ for each compound corresponds to one line of Table A Table 3
Compounds of the formula IA where m is zero, $R^2$ is ethyl and the radical $R^3$ for each compound corresponds to one line of Table A Table 4
Compounds of the formula IA where m is zero, $R^2$ is n-propyl and the radical $R^3$ for each compound corresponds to one line of Table A Table 5
Compounds of the formula IA where m is zero, $R^2$ is isopropyl and the radical $R^3$ for each compound corresponds to one line of Table A Table 6
Compounds of the formula IA where m is zero, $R^2$ is cyano and the radical $R^3$ for each compound corresponds to one line of Table A Table 7
Compounds of the formula IA where $(X)_m$ is 3-chloro, $R^2$ is hydrogen and the radical $R^3$ for each compound corresponds to one line of Table A Table 8
Compounds of the formula IA where $(X)_m$ is 3-chloro, $R^2$ is methyl and the radical $R^3$ for each compound corresponds to one line of Table A Table 9
Compounds of the formula IA where $(X)_m$ is 3-chloro, $R^2$ is ethyl and the radical $R^3$ for each compound corresponds to one line of Table A Table 10
Compounds of the formula IA where $(X)_m$ is 3-chloro, $R^2$ is n-propyl and the radical $R^3$ for each compound corresponds to one line of Table A Table 11
Compounds of the formula IA where $(X)_m$ is 3-chloro, $R^2$ is isopropyl and the radical $R^3$ for each compound corresponds to one line of Table A Table 12
Compounds of the formula IA where $(X)_m$ is 3-chloro, $R^2$ is cyano and the radical $R^3$ for each compound corresponds to one line of Table A Table 13
Compounds of the formula IA where $(X)_m$ is 4-chloro, $R^2$ is hydrogen and the radical $R^3$ for each compound corresponds to one line of Table A Table 14
Compounds of the formula IA where $(X)_m$ is 4-chloro, $R^2$ is methyl and the radical $R^3$ for each compound corresponds to one line of Table A Table 15
Compounds of the formula IA where $(X)_m$ is 4-chloro, $R^2$ is ethyl and the radical $R^3$ for each compound corresponds to one line of Table A Table 16
Compounds of the formula IA where $(X)_m$ is 4-chloro, $R^2$ is n-propyl and the radical $R^3$ for each compound corresponds to one line of Table A Table 17
Compounds of the formula IA where $(X)_m$ is 4-chloro, $R^2$ is isopropyl and the radical $R^3$ for each compound corresponds to one line of Table A Table 18
Compounds of the formula IA where $(X)_m$ is 4-chloro, $R^2$ is cyano and the radical $R^3$ for each compound corresponds to one line of Table A Table 19
Compounds of the formula IA where $(X)_m$ is 5-chloro, $R^2$ is hydrogen and the radical $R^3$ for each compound corresponds to one line of Table A Table 20
Compounds of the formula IA where $(X)_m$ is 5-chloro, $R^2$ is methyl and the radical $R^3$ for each compound corresponds to one line of Table A Table 21
Compounds of the formula IA where $(X)_m$ is 5-chloro, $R^2$ is ethyl and the radical $R^3$ for each compound corresponds to one line of Table A Table 22
Compounds of the formula IA where $(X)_m$ is 5-chloro, $R^2$ is n-propyl and the radical $R^3$ for each compound corresponds to one line of Table A Table 23
Compounds of the formula IA where $(X)_m$ is 5-chloro, $R^2$ is isopropyl and the radical $R^3$ for each compound corresponds to one line of Table A Table 24
Compounds of the formula IA where $(X)_m$ is 5-chloro, $R^2$ is cyano and the radical $R^3$ for each compound corresponds to one line of Table A Table 25
Compounds of the formula IA where $(X)_m$ is 3-bromo, $R^2$ is hydrogen and the radical $R^3$ for each compound corresponds to one line of Table A Table 26
Compounds of the formula IA where $(X)_m$ is 3-bromo, $R^2$ is methyl and the radical $R^3$ or each compound corresponds to one line of Table A Table 27
Compounds of the formula IA where $(X)_m$ is 3-bromo, $R^2$ is ethyl and the radical $R^3$ for each compound corresponds to one line of Table A Table 28
Compounds of the formula IA where $(X)_m$ is 3-bromo, $R^2$ is n-propyl and the radical $R^3$ for each compound corresponds to one line of Table A Table 29
Compounds of the formula IA where $(X)_m$ is 3-bromo, $R^2$ is isopropyl and the radical $R^3$ for each compound corresponds to one line of Table A Table 30
Compounds of the formula IA where $(X)_m$ is 3-bromo, $R^2$ is cyano and the radical $R^3$ for each compound corresponds to one line of Table A Table 31
Compounds of the formula IA where $(X)_m$ is 4-bromo, $R^2$ is hydrogen and the radical $R^3$ for each compound corresponds to one line of Table A Table 32
Compounds of the formula IA where $(X)_m$ is 4-bromo, $R^2$ is methyl and the radical $R^3$ for each compound corresponds to one line of Table A Table 33
Compounds of the formula IA where $(X)_m$ is 4-bromo, $R^2$ is ethyl and the radical $R^3$ for each compound corresponds to one line of Table A Table 34
Compounds of the formula IA where $(X)_m$ is 4-bromo, $R^2$ is n-propyl and the radical $R^3$ for each compound corresponds to one line of Table A Table 35
Compounds of the formula IA where $(X)_m$ is 4-bromo, $R^2$ is isopropyl and the radical $R^3$ for each compound corresponds to one line of Table A Table 36
Compounds of the formula IA where $(X)_m$ is 4-bromo, $R^2$ is cyano and the radical $R^3$ for each compound corresponds to one line of Table A Table 37
Compounds of the formula IA where $(X)_m$ is 5-bromo, $R^2$ is hydrogen and the radical $R^3$ for each compound corresponds to one line of Table A Table 38
Compounds of the formula IA where $(X)_m$ is 5-bromo, $R^2$ is methyl and the radical $R^3$ for each compound corresponds to one line of Table A Table 39
Compounds of the formula IA where $(X)_m$ is 5-bromo, $R^2$ is ethyl and the radical $R^3$ for each compound corresponds to one line of Table A Table 40
Compounds of the formula IA where $(X)_m$ is 5-bromo, $R^2$ is n-propyl and the radical $R^3$ for each compound corresponds to one line of Table A Table 41
Compounds of the formula IA where $(X)_m$ is 5-bromo, $R^2$ is isopropyl and the radical $R^3$ for each compound corresponds to one line of Table A Table 42
Compounds of the formula IA where $(X)_m$ is 5-bromo, $R^2$ is cyano and the radical $R^3$ for each compound corresponds to one line of Table A Table 43
Compounds of the formula IA where $(X)_m$ is 3-nitro, $R^2$ is hydrogen and the radical $R^3$ for each compound corresponds to one line of Table A Table 44
Compounds of the formula IA where $(X)_m$ is 3-nitro, $R^2$ is methyl and the radical $R^3$ for each compound corresponds to one line of Table A Table 45
Compounds of the formula IA there $(X)_m$ is 3-nitro, $R^2$ is ethyl and the radical $R^3$ for each compound corresponds to one line of Table A Table 46
Compounds of the formula IA where $(X)_m$ is 3-nitro, $R^2$ is n-propyl and the radical $R^3$ for each compound corresponds to one line of Table A Table 47
Compounds of the formula IA where $(X)_m$ is 3-nitro, $R^2$ is isopropyl and the radical $R^3$ for each compound corresponds to one line of Table A Table 48
Compounds of the formula IA where $(X)_m$ is 3-nitro, $R^2$ is cyano and the radical $R^3$ for each compound corresponds to one line of Table A Table 49
Compounds of the formula IA where $(X)_m$ is 4-nitro, $R^2$ is hydrogen and the radical $R^3$ for each compound corresponds to one line of Table A Table 50
Compounds of the formula IA where $(X)_m$ is 4-nitro, $R^2$ is methyl and the radical $R^3$ for each compound corresponds to one line of Table A Table 51
Compounds of the formula IA where $(X)_m$ is 4-nitro, $R^2$ is ethyl and the radical $R^3$ for each compound corresponds to one line of Table A Table 52
Compounds of the formula IA where $(X)_m$ is 4-nitro, $R^2$ is n-propyl and the radical $R^3$ for each compound corresponds to one line of Table A Table 53
Compounds of the formula IA where $(X)_m$ is 4-nitro, $R^2$ is isopropyl and the radical $R^3$ for each compound corresponds to one line of Table A Table 54
Compounds of the formula IA where $(X)_m$ is 4-nitro, $R^2$ is cyano and the radical $R^3$ for each compound corresponds to one line of Table A Table 55
Compounds of the formula IA where $(X)_m$ is 5-nitro, $R^2$ is hydrogen and the radical $R^3$ for each compound corresponds to one line of Table A Table 56
Compounds of the formula IA where $(X)_m$ is 5-nitro, $R^2$ is methyl and the radical $R^3$ for each compound corresponds to one line of Table A Table 57
Compounds of the formula IA where $(X)_m$ is 5-nitro, $R^2$ is ethyl and the radical $R^3$ for each compound corresponds to one line of Table A Table 58
Compounds of the formula IA where $(X)_m$ is 5-nitro, $R^2$ is n-propyl and the radical $R^3$ for each compound corresponds to one line of Table A Table 59
Compounds of the formula IA where $(X)_m$ is 5-nitro, $R^2$ is isopropyl and the radical $R^3$ for each compound corresponds to one line of Table A Table 60
Compounds of the formula IA where $(X)_m$ is 5-nitro, $R^2$ is cyano and the radical $R^3$ for each compound corresponds to one line of Table A Table 61
Compounds of the formula IB where m is zero, $R^2$ is hydrogen and the radical $R^3$ for each compound corresponds to one line of Table A

IB

Table 62
Compounds of the formula IB where m is zero, $R^2$ is methyl and the radical $R^3$ for each compound corresponds to one line of Table A Table 63
Compounds of the formula IB where m is zero, $R^2$ is ethyl and the radical $R^3$ for each compound corresponds to one line of Table A Table 64
Compounds of the formula IB where m is zero, $R^2$ is n-propyl and the radical $R^3$ for each compound corresponds to one line of Table A Table 65
Compounds of the formula IB where m is zero, $R^2$ is isopropyl and the radical $R^3$ for each compound corresponds to one line of Table A Table 66
Compounds of the formula IB where m is zero, $R^2$ is cyano and the radical $R^3$ for each compound corresponds to one line of Table A Table 67
Compounds of the formula IB where $(X)_m$ is 3-chloro, $R^2$ is hydrogen and the radical $R^3$ for each compound corresponds to one line of Table A Table 68
Compounds of the formula IB where $(X)_m$ is 3-chloro, $R^2$ is methyl and the radical $R^3$ for each compound corresponds to one line of Table A Table 69
Compounds of the formula IB where $(X)_m$ is 3-chloro, $R^2$ is ethyl and the radical $R^3$ for each compound corresponds to one line of Table A Table 70
Compounds of the formula IB where $(X)_m$ is 3-chloro, $R^2$ is n-propyl and the radical $R^3$ for each compound corresponds to one line of Table A Table 71
Compounds of the formula IB where $(X)_m$ is 3-chloro, $R^2$ is isopropyl and the radical $R^3$ for each compound corresponds to one line of Table A Table 72
Compounds of the formula IB where $(X)_m$ is 3-chloro, $R^2$ is cyano and the radical $R^3$ for each compound corresponds to one line of Table A Table 73
Compounds of the formula IB where $(X)_m$ is 4-chloro, $R^2$ is hydrogen and the radical $R^3$ for each compound corresponds to one line of Table A Table 74
Compounds of the formula IB where $(X)_m$ is 4-chloro, $R^2$ is methyl and the radical $R^3$ for each compound corresponds to one line of Table A Table 75
Compounds of the formula IB where $(X)_m$ is 4-chloro, $R^2$ is ethyl and the radical $R^3$ for each compound corresponds to one line of Table A Table 76
Compounds of the formula IB where $(X)_m$ is 4-chloro, $R^2$ is n-propyl and the radical $R^3$ for each compound corresponds to one line of Table A Table 77
Compounds of the formula IB where $(X)_m$ is 4-chloro, $R^2$ is isopropyl and the radical $R^3$ for each compound corresponds to one line of Table A Table 78
Compounds of the formula IB where $(X)_m$ is 4-chloro, $R^2$ is cyano and the radical $R^3$ for each compound corresponds to one line of Table A Table 79
Compounds of the formula IB where $(X)_m$ is 5-chloro, $R^2$ is hydrogen and the radical $R^3$ for each compound corresponds to one line of Table A Table 80
Compounds of the formula IB where $(X)_m$ is 5-chloro, $R^2$ is methyl and the radical $R^3$ for each compound corresponds to one line of Table A Table 81
Compounds of the formula IB where $(X)_m$ is 5-chloro, $R^2$ is ethyl and the radical $R^3$ for each compound corresponds to one line of Table A Table 82
Compounds of the formula IB where $(X)_m$ is 5-chloro, $R^2$ is n-propyl and the radical $R^3$ for each compound corresponds to one line of Table A Table 83
Compounds of the formula IB where $(X)_m$ is 5-chloro, $R^2$ is isopropyl and the radical $R^3$ for each compound corresponds to one line of Table A Table 84
Compounds of the formula IB where $(X)_m$ is 5-chloro, $R^2$ is cyano and the radical $R^3$ for each compound corresponds to one line of Table A Table 85
Compounds of the formula IB where $(X)_m$ is 3-bromo, $R^2$ is hydrogen and the radical $R^3$ for each compound corresponds to one line of Table A Table 86
Compounds of the formula IB where $(X)_m$ is 3-bromo, $R^2$ is methyl and the radical $R^3$ for each compound corresponds to one line of Table A Table 87
Compounds of the formula IB where $(X)_m$ is 3-bromo, $R^2$ is ethyl and the radical $R^3$ for each compound corresponds to one line of Table A Table 88
Compounds of the formula IB where $(X)_m$ is 3-bromo, $R^2$ is n-propyl and the radical $R^3$ for each compound corresponds to one line of Table A Table 89
Compounds of the formula IB where $(X)_m$ is 3-bromo, $R^2$ is isopropyl and the radical $R^3$ for each compound corresponds to one line of Table A Table 90
Compounds of the formula IB where $(X)_m$ is 3-bromo, $R^2$ is cyano and the radical $R^3$ for each compound corresponds to one line of Table A Table 91
Compounds of the formula IB where $(X)_m$ is 4-bromo, $R^2$ is hydrogen and the radical $R^3$ for each compound corresponds to one line of Table A Table 92
Compounds of the formula IB where $(X)_m$ is 4-bromo, $R^2$ is methyl and the radical $R^3$ for each compound corresponds to one line of Table A Table 93
Compounds of the formula IB where $(X)_m$ is 4-bromo, $R^2$ is ethyl and the radical $R^3$ for each compound corresponds to one line of Table A Table 94
Compounds of the formula IB where $(X)_m$ is 4-bromo, $R^2$ is n-propyl and the radical $R^3$ for each compound corresponds to one line of Table A Table 95
Compounds of the formula IB where $(X)_m$ is 4-bromo, $R^2$ is isopropyl and the radical $R^3$ for each compound corresponds to one line of Table A Table 96
Compounds of the formula IB where $(X)_m$ is 4-bromo, $R^2$ is cyano and the radical $R^3$ for each compound corresponds to one line of Table A Table 97
Compounds of the formula IB where $(X)_m$ is 5-bromo, $R^2$ is hydrogen and the radical $R^3$ for each compound corresponds to one line of Table A Table 98
Compounds of the formula IB where $(X)_m$ is 5-bromo, $R^2$ is methyl and the radical $R^3$ for each compound corresponds to one line of Table A Table 99
Compounds of the formula IB where $(X)_m$ is 5-bromo, $R^2$ is ethyl and the radical $R^3$ for each compound corresponds to one line of Table A Table 100
Compounds of the formula IB where $(X)_m$ is 5-bromo, $R^2$ is n-propyl and the radical $R^3$ for each compound corresponds to one line of Table A Table 101
Compounds of the formula IB where $(X)_m$ is 5-bromo, $R^2$ is isopropyl and the radical $R^3$ for each compound corresponds to one line of Table A Table 102
Compounds of the formula IB where $(X)_m$ is 5-bromo. $R^2$ is cyano and the radical $R^3$ for each compound corresponds to one line of Table A Table 103
Compounds of the formula IB where $(X)_m$ is 3-nitro, $R^2$ is hydrogen and the radical $R^3$ for each compound corresponds to one line of Table A Table 104
Compounds of the formula IB where $(X)_m$ is 3-nitro, $R^2$ is methyl and the radical $R^3$ for each compound corresponds to one line of Table A Table 105
Compounds of the formula IB where $(X)_m$ is 3-nitro, $R^2$ is ethyl and the radical $R^3$ for each compound corresponds to one line of Table A Table 106
Compounds of the formula IB where $(X)_m$ is 3-nitro, $R^2$ is n-propyl and the radical $R^3$ for each compound corresponds to one line of Table A Table 107
Compounds of the formula IB where $(X)_m$ is 3-nitro, $R^2$ is isopropyl and the radical $R^3$ for each compound corresponds to one line of Table A Table 108
Compounds of the formula IB where $(X)_m$ is 3-nitro, $R^2$ is cyano and the radical $R^3$ for each compound corresponds to one line of Table A Table 109
Compounds of the formula IB where $(X)_m$ is 4-nitro, $R^2$ is hydrogen and the radical $R^3$ for each compound corresponds to one line of Table A Table 110
Compounds of the formula IB where $(X)_m$ is 4-nitro, $R^2$ is methyl and the radical $R^3$ for each compound corresponds to one line of Table A Table 111
Compounds of the formula IB where $(X)_m$ is 4-nitro, $R^2$ is ethyl and the radical $R^3$ for each compound corresponds to one line of Table Table 112
Compounds of the formula IB where $(X)_m$ is 4-nitro, $R^2$ is n-propyl and the radical $R^3$ for each compound corresponds to one line of Table A Table 113
Compounds of the formula IB where $(X)_m$ is 4-nitro, $R^2$ is isopropyl and the radical $R^3$ for each compound corresponds to one line of Table A Table 114
Compounds of the formula IB where $(X)_m$ is 4-nitro, $R^2$ is cyano and the radical $R^3$ for each compound corresponds to one line of Table A Table 115
Compounds of the formula IB where $(X)_m$ is 5-nitro, $R^2$ is hydrogen and the radical $R^3$ for each compound corresponds to one line of Table A Table 116
Compounds of the formula IB where $(X)_m$ is 5-nitro, $R^2$ is methyl and the radical $R^3$ for each compound corresponds to one line of Table A Table 117
Compounds of the formula IB where $(X)_m$ is 5-nitro, $R^2$ is ethyl and the radical $R^3$ for each compound corresponds to one line of Table A Table 118
Compounds of the formula IB where $(X)_m$ is 5-nitro, $R^2$ is n-propyl and the radical $R^3$ for each compound corresponds to one line of Table A Table 119
Compounds of the formula IB where $(X)_m$ is 5-nitro, $R^2$ is isopropyl and the radical $R^3$ for each compound corresponds to one line of Table A Table 120
Compounds of the formula IB where $(X)_m$ is 5-nitro, $R^2$ is cyano and the radical $R^3$ for each compound corresponds to one line of Table A Table 121
Compounds of the formula I.1 where m is zero, $R^2$ is hydrogen and the radical $R^3$ for each compound corresponds to one line of Table A

I.1

Table 122
Compounds of the formula I.1 where m is zero, $R^2$ is methyl and the radical $R^3$ for each compound corresponds to one line of Table A Table 123
Compounds of the formula I.1 where m is zero, $R^2$ is ethyl and the radical $R^3$ for each compound corresponds to one line of Table A Table 124
Compounds of the formula I.1 where m is zero, $R^2$ is n-propyl and the radical $R^3$ for each compound corresponds to one line of Table A Table 125
Compounds of the formula I.1 where m is zero, $R^2$ is isopropyl and the radical $R^3$ for each compound corresponds to one line of Table A Table 126
Compounds of the formula I.1 where m is zero, $R^2$ is cyano and the radical $R^3$ for each compound corresponds to one line of Table A Table 127
Compounds of the formula I.1 where $(X)_m$ is 3-chloro, $R^2$ is hydrogen and the radical $R^3$ for each compound corresponds to one line of Table A Table 128
Compounds of the formula I.1 where $(X)_m$ is 3-chloro, $R^2$ is methyl and the radical $R^3$ for each compound corresponds to one line of Table A Table 129
Compounds of the formula I.1 where $(X)_m$ is 3-chloro, $R^2$ is ethyl and the radical $R^3$ for each compound corresponds to one line of Table A Table 130
Compounds of the formula I.1 where $(X)_m$ is 3-chloro, $R^2$ is n-propyl and the radical $R^3$ for each compound corresponds to one line of Table A Table 131
Compounds of the formula I.1 where $(X)_m$ is 3-chloro, $R^2$ is isopropyl and the radical $R^3$ for each compound corresponds to one line of Table A Table 132
Compounds of the formula I.1 where $(X)_m$ is 3-chloro, $R^2$ is cyano and the radical $R^3$ for each compound corresponds to one line of Table A Table 133
Compounds of the formula I.1 where $(X)_m$ is 4-chloro, $R^2$ is hydrogen and the radical $R^3$ for each compound corresponds to one line of Table A Table 134
Compounds of the formula I.1 where $(X)_m$ is 4-chloro, $R^2$ is methyl and the radical $R^3$ for each compound corresponds to one line of Table A Table 135
Compounds of the formula I.1 where $(X)_m$ is 4-chloro, $R^2$ is ethyl and the radical $R^3$ for each compound corresponds to one line of Table A Table 136
Compounds of the formula I.1 where $(X)_m$ is 4-chloro, $R^2$ is n-propyl and the radical $R^3$ for each compound corresponds to one line of Table A Table 137
Compounds of the formula I.1 where $(X)_m$ is 4-chloro, $R^2$ is isopropyl and the radical $R^3$ for each compound corresponds to one line of Table A Table 138
Compounds of the formula I.1 where $(X)_m$ is 4-chloro, $R^2$ is cyano and the radical $R^3$ for each compound corresponds to one line of Table A Table 139
Compounds of the formula I.1 where $(X)_m$ is 5-chloro, $R^2$ is hydrogen and the radical $R^3$ for each compound corresponds to one line of Table A Table 140
Compounds of the formula I.1 where $(X)_m$ is 5-chloro, $R^2$ is methyl and the radical $R^3$ for each compound corresponds to one line of Table A Table 141
Compounds of the formula I.1 where $(X)_m$ is 5-chloro, $R^2$ is ethyl and the radical $R^3$ for each compound corresponds to one line of Table A Table 142
Compounds of the formula I.1 where $(X)_m$ is 5-chloro, $R^2$ is n-propyl and the radical $R^3$ for each compound corresponds to one line of Table A Table 143
Compounds of the formula I.1 where $(X)_m$ is 5-chloro, $R^2$ is isopropyl and the radical $R^3$ for each compound corresponds to one line of Table A Table 144
Compounds of the formula I.1 where $(X)_m$ is 5-chloro, $R^2$ is cyano and the radical $R^3$ for each compound corresponds to one line of Table A Table 145
Compounds of the formula I.1 where $(X)_m$ is 3-bromo, $R^2$ is hydrogen and the radical $R^3$ for each compound corresponds to one line of Table A Table 146
Compounds of the formula I.1 where $(X)_m$ is 3-bromo, $R^2$ is methyl and the radical $R^3$ for each compound corresponds to one line of Table A Table 147
Compounds of the formula I.1 where $(X)_m$ is 3-bromo, $R^2$ is ethyl and the radical $R^3$ for each compound corresponds to one line of Table A Table 148
Compounds of the formula I.1 where $(X)_m$ is 3-bromo, $R^2$ is n-propyl and the radical $R^3$ for each compound corresponds to one line of Table A Table 149
Compounds of the formula I.1 where $(X)_m$ is 3-bromo, $R^2$ is isopropyl and the radical $R^3$ for each compound corresponds to one line of Table A Table 150
Compounds of the formula I.1 where $(X)_m$ is 3-bromo $R^2$ is cyano and the radical $R^3$ for each compound corresponds to one line of Table A Table 151
Compounds of the formula I.1 where $(X)_m$ is 4-bromo, $R^2$ is hydrogen and the radical $R^3$ for each compound corresponds to one line of Table A Table 152
Compounds of the formula I.1 where $(X)_m$ is 4-bromo, $R^2$ is methyl and the radical $R^3$ for each compound corresponds to one line of Table A Table 153
Compounds of the formula I.1 where $(X)_m$ is 4-bromo, $R^2$ is ethyl and the radical $R^3$ for each compound corresponds to one line of Table A Table 154
Compounds of the formula I.1 where $(X)_m$ is 4-bromo, $R^2$ is n-propyl and the radical $R^3$ for each compound corresponds to one line of Table A Table 155
Compounds of the formula I.1 where $(X)_m$ is 4-bromo, $R^2$ is isopropyl and the radical $R^3$ for each compound corresponds to one line of Table A Table 156
Compounds of the formula I.1 where $(X)_m$ is 4-bromo, $R^2$ is cyano and the radical $R^3$ for each compound corresponds to one line of Table A Table 157
Compounds of the formula I.1 where $(X)_m$ is 5-bromo, $R^2$ is hydrogen and the radical $R^3$ for each compound corresponds to one line of Table A Table 158
Compounds of the formula I.1 where $(X)_m$ is 5-bromo, $R^2$ is methyl and the radical $R^3$ for each compound corresponds to one line of Table A Table 159
Compounds of the formula I.1 where $(X)_m$ is 5-bromo, $R^2$ is ethyl and the radical $R^3$ for each compound corresponds to one line of Table A Table 160
Compounds of the formula I.1 where $(X)_m$ is 5-bromo, $R^2$ is n-propyl and the radical $R^3$ for each compound corresponds to one line of Table A Table 161
Compounds of the formula I.1 where $(X)_m$ is 5-bromo, $R^2$ is isopropyl and the radical $R^3$ for each compound corresponds to one line of Table A Table 162
Compounds of the formula I.1 where $(X)_m$ is 5-bromo, $R^2$ is cyano and the radical $R^3$ for each compound corresponds to one line of Table A Table 163
Compounds of the formula I.1 where $(X)_m$ is 3-nitro, $R^2$ is hydrogen and the radical $R^3$ for each compound corresponds to one line of Table A Table 164
Compounds of the formula I.1 where $(X)_m$ is 3-nitro, $R^2$ is methyl and the radical $R^3$ for each compound corresponds to one line of Table A Table 165
Compounds of the formula I.1 where $(X)_m$ is 3-nitro, $R^2$ is ethyl and the radical $R^3$ for each compound corresponds to one line of Table A Table 166
Compounds of the formula I.1 where $(X)_m$ is 3-nitro, $R^2$ is n-propyl and the radical $R^3$ for each compound corresponds to one line of Table A Table 167
Compounds of the formula I.1 where $(X)_m$ is 3-nitro, $R^2$ is isopropyl and the radical $R^3$ for each compound corresponds to one line of Table A Table 168
Compounds of the formula I.1 where $(X)_m$ is 3-nitro, $R^2$ is cyano and the radical $R^3$ for each compound corresponds to one line of Table A Table 169
Compounds of the formula I.1 where $(X)_m$ is 4-nitro, $R^2$ is hydrogen and the radical $R^3$ for each compound corresponds to one line of Table A Table 170
Compounds of the formula I.1 where $(X)_m$ is 4-nitro, $R^2$ is methyl and the radical $R^3$ for each compound corresponds to one line of Table A Table 171
Compounds of the formula I.1 where $(X)_m$ is 4-nitro, $R^2$ is ethyl and the radical $R^3$ for each compound corresponds to one line of Table A Table 172
Compounds of the formula I.1 where $(X)_m$ is 4-nitro, $R^2$ is n-propyl and the radical $R^3$ for each compound corresponds to one line of Table A Table 173
Compounds of the formula I.1 where $(X)_m$ is 4-nitro, $R^2$ is isopropyl and the radical $R^3$ for each compound corresponds to one line of Table A Table 174
Compounds of the formula I.1 where $(X)_m$ is 4-nitro, $R^2$ is cyano and the radical $R^3$ for each compound corresponds to one line of Table A Table 175
Compounds of the formula I.1 where $(X)_m$ is 5-nitro, $R^2$ is hydrogen and the radical $R^3$ for each compound corresponds to one line of Table A Table 176
Compounds of the formula I.1 where $(X)_m$ is 5-nitro, $R^2$ is methyl and the radical $R^3$ for each compound corresponds to one line of Table A Table 177
Compounds of the formula I.1 where $(X)_m$ is 5-nitro, $R^2$ is ethyl and the radical $R^3$ for each compound corresponds to one line of Table A Table 178
Compounds of the formula I.1 where $(X)_m$ is 5-nitro, $R^2$ is n-propyl and the radical $R^2$ for each compound corresponds to one line of Table A Table 179
Compounds of the formula I.1 where $(X)_m$ is 5-nitro, $R^2$ is isopropyl and the radical $R^3$ for each compound corresponds to one line of Table A Table 180
Compounds of the formula I.1 where $(X)_m$ is 5-nitro, $R^2$ is cyano and the radical $R^3$ for each compound corresponds to one line of Table A Table 181
Compounds of the formula I.2 where m is zero, $R^2$ is hydrogen and the radical $R^3$ for each compound corresponds to one line of Table A $$\text{I.2}$$

Table 182
Compounds of the formula I.2 where m is zero, $R^2$ is methyl and the radical $R^3$ for each compound corresponds to one line of Table A Table 183
Compounds of the formula I.2 where m is zero, $R^2$ is ethyl and the radical $R^3$ for each compound corresponds to one line of Table A Table 184
Compounds of the formula I.2 where m is zero, $R^2$ is n-propyl and the radical $R^3$ for each compound corresponds to one line of Table A Table 185
Compounds of the formula I.2 where m is zero, $R^2$ is isopropyl and the radical $R^3$ for each compound corresponds to one line of Table A Table 186
Compounds of the formula I.2 where m is zero, $R^2$ is cyano and the radical $R^3$ for each compound corresponds to one line of Table A Table 187
Compounds of the formula I.2 where $(X)_m$ is 3-chloro, $R^2$ is hydrogen and the radical $R^3$ for each compound corresponds to one line of Table A Table 188
Compounds of the formula I.2 where $(X)_m$ is 3-chloro, $R^2$ is methyl and the radical $R^3$ for each compound corresponds to one line of Table A Table 189
Compounds of the formula I.2 where $(X)_m$ is 3-chloro, $R^2$ is ethyl and the radical $R^3$ for each compound corresponds to one line of Table A Table 190
Compounds of the formula I.2 where $(X)_m$ is 3-chloro, $R^2$ is n-propyl and the radical $R^3$ for each compound corresponds to one line of Table A Table 191
Compounds of the formula I.2 where $(X)_m$ is 3-chloro, $R^2$ is isopropyl and the radical $R^3$ for each compound corresponds to one line of Table A Table 192
Compounds of the formula I.2 where $(X)_m$ is 3-chloro, $R^2$ is cyano and the radical $R^3$ for each compound corresponds to one line of Table A Table 193
Compounds of the formula I.2 where $(X)_m$ is 4-chloro, $R^2$ is hydrogen and the radical $R^3$ for each compound corresponds to one line of Table A Table 194
Compounds of the formula I.2 where $(X)_m$ is 4-chloro, $R^2$ is methyl and the radical $R^2$ for each compound corresponds to one line of Table A Table 195
Compounds of the formula I.2 where $(X)_m$ is 4-chloro, $R^2$ is ethyl and the radical $R^3$ for each compound corresponds to one line of Table A Table 196
Compounds of the formula I.2 where $(X)_m$ is 4-chloro, $R^2$ is n-propyl and the radical $R^3$ for each compound corresponds to one line of Table A Table 197
Compounds of the formula I.2 where $(X)_m$ is 4-chloro, $R^2$ is isopropyl and the radical $R^3$ for each compound corresponds to one line of Table A Table 198
Compounds of the formula I.2 where $(X)_m$ is 4-chloro, $R^2$ is cyano and the radical $R^3$ for each compound corresponds to one line of Table A Table 199
Compounds of the formula I.2 where $(X)_m$ is 5-chloro, $R^2$ is hydrogen and the radical $R^3$ for each compound corresponds to one line of Table A Table 200
Compounds of the formula I.2 where $(X)_m$ is 5-chloro, $R^2$ is methyl and the radical $R^3$ for each compound corresponds to one line of Table A Table 201
Compounds of the formula I.2 where $(X)_m$ is 5-chloro, $R^2$ is ethyl and the radical $R^3$ for each compound corresponds to one line of Table A Table 202
Compounds of the formula I.2 where $(X)_m$ is 5-chloro, $R^2$ is n-propyl and the radical $R^3$ for each compound corresponds to one line of Table A Table 203
Compounds of the formula I.2 where $(X)_m$ is 5-chloro, $R^2$ is isopropyl and the radical $R^3$ for each compound corresponds to one line of Table A Table 204
Compounds of the formula I.2 where $(X)_m$ is 5-chloro, $R^2$ is cyano and the radical $R^2$ for each compound corresponds to one line of Table A Table 205
Compounds of the formula I.2 where $(X)_m$ is 3-bromo, $R^2$ is hydrogen and the radical $R^3$ for each compound corresponds to one line of Table A Table 206
Compounds of the formula I.2 where $(X)_m$ is 3-bromo, $R^2$ is methyl and the radical $R^3$ for each compound corresponds to one line of Table A Table 207
Compounds of the formula I.2 where $(X)_m$ is 3-bromo, $R^2$ is ethyl and the radical $R^3$ for each compound corresponds to one line of Table A Table 208
Compounds of the formula I.2 where $(X)_m$ is 3-bromo, $R^2$ is n-propyl and the radical $R^3$ for each compound corresponds to one line of Table A Table 209
Compounds of the formula I.2 where $(X)_m$ is 3-bromo, $R^2$ is isopropyl and the radical $R^3$ for each compound corresponds to one line of Table A Table 210
Compounds of the formula I.2 where $(X)_m$ is 3-bromo, $R^2$ is cyano and the radical $R^3$ for each compound corresponds to one line of Table A Table 211
Compounds of the formula I.2 where $(X)_m$ is 4-bromo, 2 is hydrogen and the radical $R^3$ for each compound corresponds to one line of Table A Table 212
Compounds of the formula I.2 where $(X)_m$ is 4-bromo, $R^2$ is methyl and the radical $R^3$ for each compound corresponds to one line of Table A Table 213
Compounds of the formula I.2 where $(X)_m$ is 4-bromo, $R^2$ is ethyl and the radical $R^3$ for each compound corresponds to one line of Table A Table 214
Compounds of the formula I.2 where $(X)_m$ is 4-bromo, $R^2$ is n-propyl and the radical $R^3$ for each compound corresponds to one line of Table A Table 215
Compounds of the formula I.2 where $(X)_m$ is 4-bromo, $R^2$ is isopropyl and the radical $R^3$ for each compound corresponds to one line of Table A Table 216
Compounds of the formula I.2 where $(X)_m$ is 4-bromo, $R^2$ is cyano and the radical $R^3$ for each compound corresponds to one line of Table A Table 217
Compounds of the formula I.2 where $(X)_m$ is 5-bromo, $R^2$ is hydrogen and the radical $R^3$ for each compound corresponds to one line of Table A Table 218
Compounds of the formula I.2 where $(X)_m$ is 5-bromo, $R^2$ is methyl and the radical $R^3$ for each compound corresponds to one line of Table A Table 219
Compounds of the formula I.2 where $(X)_m$ is 5-bromo, $R^2$ is ethyl and the radical $R^3$ for each compound corresponds to one line of Table A Table 220
Compounds of the formula I.2 where $(X)_m$ is 5-bromo, $R^2$ is n-propyl and the radical $R^3$ for each compound corresponds to one line of Table A Table 221
Compounds of the formula I.2 where $(X)_m$ is 5-bromo, $R^2$ is isopropyl and the radical $R^3$ for each compound corresponds to one line of Table A Table 222
Compounds of the formula I.2 where $(X)_m$ is 5-bromo, $R^2$ is cyano and the radical $R^3$ for each compound corresponds to one line of Table A Table 223
Compounds of the formula I.2 where $(X)_m$ is 3-nitro, $R^2$ is hydrogen and the radical $R^3$ for each compound corresponds to one line of Table A Table 224
Compounds of the formula I.2 where $(X)_m$ is 3-nitro, $R^2$ is methyl and the radical $R^3$ for each compound corresponds to one line of Table A Table 225
Compounds of the formula I.2 where $(X)_m$ is 3-nitro, $R^2$ is ethyl and the radical $R^3$ for each compound corresponds to one line of Table A Table 226
Compounds of the formula I.2 where $(X)_m$ is 3-nitro, $R^2$ is n-propyl and the radical $R^3$ for each compound corresponds to one line of Table A Table 227
Compounds of the formula I.2 where $(X)_m$ is 3-nitro, $R^2$ is isopropyl and the radical $R^3$ for each compound corresponds to one line of Table A Table 228
Compounds of the formula I.2 where $(X)_m$ is 3-nitro, $R^2$ is cyano and the radical $R^3$ for each compound corresponds to one line of Table A Table 229
Compounds of the formula I.2 where $(X)_m$ is 4-nitro, $R^2$ is hydrogen and the radical $R^3$ for each compound corresponds to one line of Table A Table 230
Compounds of the formula I.2 where $(X)_m$ is 4-nitro, $R^2$ is methyl and the radical $R^3$ for each compound corresponds to one line of Table A Table 231
Compounds of the formula I.2 where $(X)_m$ is 4-nitro, $R^2$ is ethyl and the radical $R^3$ for each compound corresponds to one line of Table A Table 232
Compounds of the formula I.2 where $(X)_m$ is 4-nitro, $R^2$ is n-propyl and the radical $R^3$ for each compound corresponds to one line of Table A Table 233
Compounds of the formula I.2 where $(X)_m$ is 4-nitro, $R^2$ is isopropyl and the radical $R^3$ for each compound corresponds to one line of Table A Table 234
Compounds of the formula I.2 where $(X)_m$ is 4-nitro, $R^2$ is cyano and the radical $R^3$ for each compound corresponds to one line of Table A Table 235
Compounds of the formula I.2 where $(X)_m$ is 5-nitro, $R^2$ is hydrogen and the radical $R^3$ for each compound corresponds to one line of Table A Table 236
Compounds of the formula I.2 where $(X)_m$ is 5-nitro, $R^2$ is methyl and the radical $R^3$ for each compound corresponds to one line of Table A Table 237
Compounds of the formula I.2 where $(X)_m$ is 5-nitro, $R^2$ is ethyl and the radical $R^3$ for each compound corresponds to one line of Table A Table 238
Compounds of the formula I.2 where $(X)_m$ is 5-nitro, $R^2$ is n-propyl and the radical $R^3$ for each compound corresponds to one line of Table A Table 239
Compounds of the formula I.2 where $(X)_m$ is 5-nitro, $R^2$ is isopropyl and the radical $R^3$ for each compound corresponds to one line of Table A Table 240
Compounds of the formula I.2 where $(X)_m$ is 5-nitro, $R^2$ is cyano and the radical $R^3$ for each compound corresponds to one line of Table A Table 241
Compounds of the formula I.3 where m is zero, $R^2$ is hydrogen and the radical $R^3$ for each compound corresponds to one line of Table A

I.3

Table 242
Compounds of the formula I.3 where m is zero, $R^2$ is methyl and the radical $R^3$ for each compound corresponds to one line of Table A Table 243
Compounds of the formula I.3 where m is zero, $R^2$ is ethyl and the radical $R^3$ for each compound corresponds to one line of Table A Table 244
Compounds of the formula I.3 where m is zero, $R^2$ is n-propyl and the radical $R^3$ for each compound corresponds to one line of Table A Table 245
Compounds of the formula I.3 where m is zero, $R^2$ is isopropyl and the radical $R^3$ for each compound corresponds to one line of Table A Table 246
Compounds of the formula I.3 where m is zero, $R^2$ is cyano and the radical $R^3$ for each compound corresponds to one line of Table A Table 247
Compounds of the formula I.3 where $(X)_m$ is 3-chloro, $R^2$ is hydrogen and the radical $R^3$ for each compound corresponds to one line of Table A Table 248
Compounds of the formula I.3 where $(X)_m$ is 3-chloro, $R^2$ is methyl and the radical $R^3$ for each compound corresponds to one line of Table A Table 249
Compounds of the formula I.3 where $(X)_m$ is 3-chloro, $R^2$ is ethyl and the radical $R^3$ for each compound corresponds to one line of Table A Table 250
Compounds of the formula I.3 where $(X)_m$ is 3-chloro, $R^2$ is n-propyl and the radical $R^3$ for each compound corresponds to one line of Table A Table 251
Compounds of the formula I.3 there $(X)_m$ is 3-chloro, $R^2$ is isopropyl and the radical $R^3$ for each compound corresponds to one line of Table A Table 252
Compounds of the formula I.3 where $(X)_m$ is 3-chloro, $R^2$ is cyano and the radical $R^3$ for each compound corresponds to one line of Table A Table 253
Compounds of the formula I.3 where $(X)_m$ is 4-chloro, $R^2$ is hydrogen and the radical $R^3$ for each compound corresponds to one line of Table A Table 254
Compounds of the formula I.3 where $(X)_m$ is 4-chloro, $R^2$ is methyl and the radical $R^3$ for each compound corresponds to one line of Table A Table 255
Compounds of the formula I.3 where $(X)_m$ is 4-chloro, $R^2$ is ethyl and the radical $R^3$ for each compound corresponds to one line of Table A Table 256
Compounds of the formula I.3 where $(X)_m$ is 4-chloro, $R^2$ is n-propyl and the radical $R^3$ for each compound corresponds to one line of Table A Table 257
Compounds of the formula I.3 where $(X)_m$ is 4-chloro, $R^2$ is isopropyl and the radical $R^3$ for each compound corresponds to one line of Table A Table 258
Compounds of the formula I.3 where $(X)_m$ is 4-chloro, $R^2$ is cyano and the radical $R^3$ for each compound corresponds to one line of Table A Table 259
Compounds of the formula I.3 where $(X)_m$ is 5-chloro, $R^2$ is hydrogen and the radical $R^3$ for each compound corresponds to one line of Table A Table 260
Compounds of the formula I.3 where $(X)_m$ is 5-chloro, $R^2$ is methyl and the radical $R^3$ for each compound corresponds to one line of Table A Table 261
Compounds of the formula I.3 where $(X)_m$ is 5-chloro, $R^2$ is ethyl and the radical $R^3$ for each compound corresponds to one line of Table A Table 262
Compounds of the formula I.3 where $(X)_m$ is 5-chloro, $R^2$ is n-propyl and the radical $R^3$ for each compound corresponds to one line of Table A Table 263
Compounds of the formula I.3 where $(X)_m$ is 5-chloro, $R^2$ is isopropyl and the radical $R^3$ for each compound corresponds to one line of Table A Table 264
Compounds of the formula I.3 where $(X)_m$ is 5-chloro, $R^2$ is cyano and the radical $R^3$ for each compound corresponds to one line of Table A Table 265
Compounds of the formula I.3 where $(X)_m$ is 3-bromo, $R^2$ is hydrogen and the radical $R^3$ for each compound corresponds to one line of Table A Table 266
Compounds of the formula I.3 where $(X)_m$ is 3-bromo, $R^2$ is methyl and the radical $R^3$ for each compound corresponds to one line of Table A Table 267
Compounds of the formula I.3 where $(X)_m$ is 3-bromo, $R^2$ is ethyl and the radical $R^3$ for each compound corresponds to one line of Table A Table 268
Compounds of the formula I.3 where $(X)_m$ is 3-bromo, $R^2$ is n-propyl and the radical $R^3$ for each compound corresponds to one line of Table A Table 269
Compounds of the formula I.3 where $(X)_m$ is 3-bromo, $R^2$ as isopropyl and the radical $R^3$ for each compound corresponds to one line of Table A Table 270
Compounds of the formula I.3 where $(X)_m$ is 3-bromo, $R^2$ is cyano and the radical $R^3$ for each compound corresponds to one line of Table A Table 271
Compounds of the formula I.3 where $(X)_m$ is 4-bromo, $R^2$ is hydrogen and the radical $R^3$ for each compound corresponds to one line of Table A Table 272
Compounds of the formula I.3 where $(X)_m$ is 4-bromo, $R^2$ is methyl and the radical $R^3$ for each compound corresponds to one line of Table A Table 273
Compounds of the formula I.3 where $(X)_m$ is 4-bromo, $R^2$ is ethyl and the radical $R^3$ for each compound corresponds to one line of Table A Table 274
Compounds of the formula I.3 where $(X)_m$ is 4-bromo, $R^2$ is n-propyl and the radical $R^3$ for each compound corresponds to one line of Table A Table 275
Compounds of the formula I.3 where $(X)_m$ is 4-bromo, $R^2$ is isopropyl and the radical $R^3$ for each compound corresponds to one line of Table A Table 276
Compounds of the formula I.3 where $(X)_m$ is 4-bromo, $R^2$ is cyano and the radical $R^3$ for each compound corresponds to one line of Table A Table 277
Compounds of the formula I.3 where $(X)_m$ is 5-bromo, $R^2$ is hydrogen and the radical $R^3$ for each compound corresponds to one line of Table A Table 278
Compounds of the formula I.3 where $(X)_m$ is 5-bromo, $R^2$ is methyl and the radical $R^3$ for each compound corresponds to one line of Table A Table 279
Compounds of the formula I.3 where $(X)_m$ is 5-bromo, $R^2$ is ethyl and the radical $R^3$ for each compound corresponds to one line of Table A Table 280
Compounds of the formula I.3 where $(X)_m$ is 5-bromo, $R^2$ is n-propyl and the radical $R^3$ for each compound corresponds to one line of Table A Table 281
Compounds of the formula I.3 where $(X)_m$ is 5-bromo, $R^2$ is isopropyl and the radical $R^3$ for each compound corresponds to one line of Table A Table 282
Compounds of the formula I.3 where $(X)_m$ is 5-bromo, $R^2$ is cyano and the radical $R^3$ for each compound corresponds to one line of Table A Table 283
Compounds of the formula I.3 where $(X)_m$ is 3-nitro, $R^2$ is hydrogen and the radical $R^3$ for each compound corresponds to one line of Table A Table 284
Compounds of the formula I.3 where $(X)_m$ is 3-nitro, $R^2$ is methyl and the radical $R^3$ for each compound corresponds to one line of Table A Table 285
Compounds of the formula I.3 where $(X)_m$ is 3-nitro, $R^2$ is ethyl and the radical $R^3$ for each compound corresponds to one line of Table A Table 286
Compounds of the formula I.3 where $(X)_m$ is 3-nitro, $R^2$ is n-propyl and the radical $R^3$ for each compound corresponds to one line of Table A Table 287
Compounds of the formula I.3 where $(X)_m$ is 3-nitro, $R^2$ is isopropyl and the radical $R^3$ for each compound corresponds to one line of Table A Table 288
Compounds of the formula I.3 where $(X)_m$ is 3-nitro, $R^2$ is cyano and the radical $R^3$ for each compound corresponds to one line of Table A Table 289
Compounds of the formula I.3 where $(X)_m$ is 4-nitro, $R^2$ is hydrogen and the radical $R^3$ for each compound corresponds to one line of Table A Table 290
Compounds of the formula I.3 where $(X)_m$ is 4-nitro, $R^2$ is methyl and the radical $R^3$ for each compound corresponds to one line of Table A Table 291
Compounds of the formula I.3 where $(X)_m$ is 4-nitro, $R^2$ is ethyl and the radical $R^3$ for each compound corresponds to one line of Table A Table 292
Compounds of the formula I.3 where $(X)_m$ is 4-nitro, $R^2$ is n-propyl and the radical $R^3$ for each compound corresponds to one line of Table A Table 293
Compounds of the formula I.3 where $(X)_m$ is 4-nitro, $R^2$ is isopropyl and the radical $R^3$ for each compound corresponds to one line of Table A Table 294
Compounds of the formula I.3 where $(X)_m$ is 4-nitro, $R^2$ is cyano and the radical $R^3$ for each compound corresponds to one line of Table A Table 295
Compounds of the formula I.3 where $(X)_m$ is 5-nitro, $R^2$ is hydrogen and the radical $R^3$ for each compound corresponds to one line of Table A Table 296
Compounds of the formula I.3 where $(X)_m$ is 5-nitro, $R^2$ is methyl and the radical $R^3$ for each compound corresponds to one line of Table A Table 297
Compounds of the formula I.3 where $(X)_m$ is 5-nitro, $R^2$ is ethyl and the radical $R^3$ for each compound corresponds to one line of Table A Table 298
Compounds of the formula I.3 where $(X)_m$ is 5-nitro, $R^2$ is n-propyl and the radical $R^3$ for each compound corresponds to one line of Table A Table 299
Compounds of the formula I.3 where $(X)_m$ is 5-nitro, $R^2$ is isopropyl and the radical $R^3$ for each compound corresponds to one line of Table A Table 300
Compounds of the formula I.3 where $(X)_m$ is 5-nitro, $R^2$ is cyano and the radical $R^3$ for each compound corresponds to one line of Table A Table 301
Compounds of the formula I.5 where m is zero, $R^2$ is hydrogen and the radical $R^3$ for each compound corresponds to one line of Table A

I.5

Table 302
Compounds of the formula I.5 where m is zero, $R^2$ is methyl and the radical $R^3$ for each compound corresponds to one line of Table A Table 303
Compounds of the formula I.5 where m is zero, $R^2$ is ethyl and the radical $R^3$ for each compound corresponds to one line of Table A Table 304
Compounds of the formula I.5 where m is zero, $R^2$ is n-propyl and the radical $R^3$ for each compound corresponds to one line of Table A Table 305
Compounds of the formula I.5 where m is zero, $R^2$ is isopropyl and the radical $R^3$ for each compound corresponds to one line of Table A Table 306
Compounds of the formula I.5 where m is zero, $R^2$ is cyano and the radical $R^3$ for each compound corresponds to one line of Table A Table 307
Compounds of the formula I.5 where $(X)_m$ is 3-chloro, $R^2$ is hydrogen and the radical $R^3$ for each compound corresponds to one line of Table A Table 308
Compounds of the formula I.5 where $(X)_m$ is 3-chloro, $R^2$ is methyl and the radical $R^3$ for each compound corresponds to one line of Table A Table 309
Compounds of the formula I.5 where $(X)_m$ is 3-chloro, $R^2$ is ethyl and the radical $R^3$ for each compound corresponds to one line of Table A Table 310
Compounds of the formula I.5 where $(X)_m$ is 3-chloro, $R^2$ is n-propyl and the radical $R^3$ for each compound corresponds to one line of Table A Table 311
Compounds of the formula I.5 where $(X)_m$ is 3-chloro, $R^2$ is isopropyl and the radical $R^3$ for each compound corresponds to one line of Table A Table 312
Compounds of the formula I.5 where $(X)_m$ is 3-chloro, $R^2$ is cyano and the radical $R^3$ for each compound corresponds to one line of Table A Table 313
Compounds of the formula I.5 where $(X)_m$ is 4-chloro, $R^2$ is hydrogen and the radical $R^2$ for each compound corresponds to one line of Table A Table 314
Compounds of the formula I.5 where $(X)_m$ is 4-chloro, $R^2$ is methyl and the radical $R^3$ for each compound corresponds to one line of Table A Table 315
Compounds of the formula I.5 where $(X)_m$ is 4-chloro, $R^2$ is ethyl and the radical $R^3$ for each compound corresponds to one line of Table A Table 316
Compounds of the formula I.5 where $(X)_m$ is 4-chloro, $R^2$ is n-propyl and the radical $R^3$ for each compound corresponds to one line of Table A Table 317
Compounds of the formula I.5 where $(X)_m$ is 4-chloro, $R^2$ is isopropyl and the radical $R^3$ for each compound corresponds to one line of Table A Table 318
Compounds of the formula I.5 where $(X)_m$ is 4-chloro, $R^2$ is cyano and the radical $R^3$ for each compound corresponds to one line of Table A Table 319
Compounds of the formula I.5 where $(X)_m$ is 5-chloro, $R^2$ is hydrogen and the radical $R^3$ for each compound corresponds to one line of Table A Table 320
Compounds of the formula I.5 where $(X)_m$ is 5-chloro, $R^2$ is methyl and the radical $R^3$ for each compound corresponds to one line of Table A Table 321
Compounds of the formula I.5 where $(X)_m$ is 5-chloro, $R^2$ is ethyl and the radical $R^3$ for each compound corresponds to one line of Table A Table 322
Compounds of the formula I.5 where $(X)_m$ is 5-chloro, $R^2$ is n-propyl and the radical $R^3$ for each compound corresponds to one line of Table A Table 323
Compounds of the formula I.5 where $(X)_m$ is 5-chloro, $R^2$ is isopropyl and the radical $R^3$ for each compound corresponds to one line of Table A Table 324
Compounds of the formula I.5 where $(X)_m$ is 5-chloro, $R^2$ is cyano and the radical $R^3$ for each compound corresponds to one line of Table A Table 325
Compounds of the formula I.5 where $(X)_m$ is 3-bromo, $R^2$ is hydrogen and the radical $R^3$ for each compound corresponds to one line of Table A Table 326
Compounds of the formula I.5 where $(X)_m$ is 3-bromo, $R^2$ is methyl and the radical $R^3$ for each compound corresponds to one line of Table A Table 327
Compounds of the formula I.5 where $(X)_m$ is 3-bromo, $R^2$ is ethyl and the radical $R^3$ for each compound corresponds to one line of Table A Table 328
Compounds of the formula I.5 where $(X)_m$ is 3-bromo, $R^2$ is n-propyl and the radical $R^3$ for each compound corresponds to one line of Table A Table 329
Compounds of the formula I.5 where $(X)_m$ is 3-bromo, $R^2$ is isopropyl and the radical $R^3$ for each compound corresponds to one line of Table A Table 330
Compounds of the formula I.5 where $(X)_m$ is 3-bromo, $R^2$ is cyano and the radical $R^3$ for each compound corresponds to one line of Table A Table 331
Compounds of the formula I.5 where $(X)_m$ is 4-bromo, $R^2$ is hydrogen and the radical $R^3$ for each compound corresponds to one line of Table A Table 332
Compounds of the formula I.5 where $(X)_m$ is 4-bromo, $R^2$ is methyl and the radical $R^3$ for each compound corresponds to one line of Table A Table 333
Compounds of the formula I.5 where $(X)_m$ is 4-bromo, $R^2$ is ethyl and the radical $R^3$ for each compound corresponds to one line of Table A Table 334
Compounds of the formula I.5 where $(X)_m$ is 4-bromo, $R^2$ is n-propyl and the radical $R^3$ for each compound corresponds to one line of Table A Table 335
Compounds of the formula I.5 where $(X)_m$ is 4-bromo, $R^2$ is isopropyl and the radical $R^3$ for each compound corresponds to one line of Table A Table 336
Compounds of the formula I.5 where $(X)_m$ is 4-bromo, $R^2$ is cyano and the radical $R^3$ for each compound corresponds to one line of Table A Table 337
Compounds of the formula I.5 where $(X)_m$ is 5-bromo, $R^2$ is hydrogen and the radical $R^3$ for each compound corresponds to one line of Table A Table 338
Compounds of the formula I.5 where $(X)_m$ is 5-bromo, $R^2$ is methyl and the radical $R^3$ for each compound corresponds to one line of Table A Table 339
Compounds of the formula I.5 where $(X)_m$ is 5-bromo, $R^2$ is ethyl and the radical $R^3$ for each compound corresponds to one line of Table A Table 340
Compounds of the formula I.5 where $(X)_m$ is 5-bromo, $R^2$ is n-propyl and the radical $R^3$ for each compound corresponds to one line of Table A Table 341
Compounds of the formula I.5 where $(X)_m$ is 5-bromo, $R^2$ is isopropyl and the radical $R^3$ for each compound corresponds to one line of Table A Table 342
Compounds of the formula I.5 where $(X)_m$ is 5-bromo, $R^2$ is cyano and the radical $R^3$ for each compound corresponds to one line of Table A Table 343
Compounds of the formula I.5 where $(X)_m$ is 3-nitro, $R^2$ is hydrogen and the radical $R^3$ for each compound corresponds to one line of Table A Table 344
Compounds of the formula I.5 where $(X)_m$ is 3-nitro, $R^2$ is methyl and the radical $R^3$ for each compound corresponds to one line of Table A Table 345
Compounds of the formula I.5 where $(X)_m$ is 3-nitro, $R^2$ is ethyl and the radical $R^3$ for each compound corresponds to one line of Table A Table 346
Compounds of the formula I.5 where $(X)_m$ is 3-nitro, $R^2$ is n-propyl and the radical $R^3$ for each compound corresponds to one line of Table A Table 347
Compounds of the formula I.5 where $(X)_m$ is 3-nitro, $R^2$ is isopropyl and the radical $R^3$ for each compound corresponds to one line of Table A Table 348
Compounds of the formula I.5 where $(X)_m$ is 3-nitro, $R^2$ is cyano and the radical $R^3$ for each compound corresponds to one line of Table A Table 349
Compounds of the formula I.5 where $(X)_m$ is 4-nitro, $R^2$ is hydrogen and the radical $R^3$ for each compound corresponds to one line of Table A Table 350
Compounds of the formula I.5 where $(X)_m$ is 4-nitro, $R^2$ is methyl and the radical $R^3$ for each compound corresponds to one line of Table A Table 351
Compounds of the formula I.5 where $(X)_m$ is 4-nitro, $R^2$ is ethyl and the radical $R^3$ for each compound corresponds to one line of Table A Table 352
Compounds of the formula I.5 where $(X)_m$ is 4-nitro, $R^2$ is n-propyl and the radical $R^3$ for each compound corresponds to one line of Table A Table 353
Compounds of the formula I.5 where $(X)_m$ is 4-nitro, $R^2$ is isopropyl and the radical $R^3$ for each compound corresponds to one line of Table A Table 354
Compounds of the formula I.5 where $(X)_m$ is 4-nitro, $R^2$ is cyano and the radical $R^3$ for each compound corresponds to one line of Table A Table 355
Compounds of the formula I.5 where $(X)_m$ is 5-nitro, $R^2$ is hydrogen and the radical $R^3$ for each compound corresponds to one line of Table A Table 356
Compounds of the formula I.5 where $(X)_m$ is 5-nitro, $R^2$ is methyl and the radical $R^3$ for each compound corresponds to one line of Table A Table 357
Compounds of the formula I.5 where $(X)_m$ is 5-nitro, $R^2$ is ethyl and the radical $R^3$ for each compound corresponds to one line of Table A Table 358
Compounds of the formula I.5 where $(X)_m$ is 5-nitro, $R^2$ is n-propyl and the radical $R^3$ for each compound corresponds to one line of Table A Table 359
Compounds of the formula I.5 where $(X)_m$ is 5-nitro, $R^2$ is isopropyl and the radical $R^3$ for each compound corresponds to one line of Table A Table 360
Compounds of the formula I.5 where $(X)_m$ is 5-nitro, $R^2$ is cyano and the radical $R^3$ for each compound corresponds to one line of Table A Table 361
Compounds of the formula I.6a where m is zero, $R^2$ is hydrogen and the radical $R^3$ for each compound corresponds to one line of Table A $$I.6a$$

Table 362
Compounds of the formula I.6a where m is zero, $R^2$ is methyl and the radical $R^3$ for each compound corresponds to one line of Table A Table 363
Compounds of the formula I.6a where m is zero, $R^2$ is ethyl and the radical $R^3$ for each compound corresponds to one line of Table A Table 364
Compounds of the formula I.6a where m is zero, $R^2$ is n-propyl and the radical $R^3$ for each compound corresponds to one line of Table A Table 365
Compounds of the formula I.6a where m is zero, $R^2$ is isopropyl and the radical $R^3$ for each compound corresponds to one line of Table A Table 366
Compounds of the formula I.6a where m is zero, $R^2$ is cyano and the radical $R^3$ for each compound corresponds to one line of Table A Table 367
Compounds of the formula I.6a where $(X)_m$ is 3-chloro, $R^2$ is hydrogen and the radical $R^3$ for each compound corresponds to one line of Table A Table 368
Compounds of the formula I.6a where $(X)_m$ is 3-chloro, $R^2$ is methyl and the radical $R^3$ for each compound corresponds to one line of Table A Table 369
Compounds of the formula I.6a where $(X)_m$ is 3-chloro, $R^2$ is ethyl and the radical $R^3$ for each compound corresponds to one line of Table A Table 370
Compounds of the formula I.6a where $(X)_m$ is 3-chloro, $R^2$ is n-propyl and the radical $R^3$ for each compound corresponds to one line of Table A Table 371
Compounds of the formula I.6a where $(X)_m$ is 3-chloro, $R^2$ is isopropyl and the radical $R^3$ for each compound corresponds to one line of Table A Table 372
Compounds of the formula I.6a where $(X)_m$ is 3-chloro, $R^2$ is cyano and the radical $R^3$ for each compound corresponds to one line of Table A Table 373
Compounds of the formula I.6a where $(X)_m$ is 4-chloro, $R^2$ is hydrogen and the radical $R^3$ for each compound corresponds to one line of Table A Table 374
Compounds of the formula I.6a where $(X)_m$ is 4-chloro, $R^2$ is methyl and the radical $R^3$ for each compound corresponds to one line of Table A Table 375
Compounds of the formula I.6a where $(X)_m$ is 4-chloro, $R^2$ is ethyl and the radical $R^3$ for each compound corresponds to one line of Table A Table 376
Compounds of the formula I.6a where $(X)_m$ is 4-chloro, $R^2$ is n-propyl and the radical $R^3$ for each compound corresponds to one line of Table A Table 377
Compounds of the formula I.6a where $(X)_m$ is 4-chloro, $R^2$ is isopropyl and the radical $R^3$ for each compound corresponds to one line of Table A Table 378
Compounds of the formula I.6a where $(X)_m$ is 4-chloro, $R^2$ is cyano and the radical $R^3$ for each compound corresponds to one line of Table A Table 379
Compounds of the formula I.6a where $(X)_m$ is 5-chloro, $R^2$ is hydrogen and the radical $R^3$ for each compound corresponds to one line of Table A Table 380
Compounds of the formula I.6a where $(X)_m$ is 5-chloro, $R^2$ is methyl and the radical $R^3$ for each compound corresponds to one line of Table A Table 381
Compounds of the formula I.6a where $(X)_m$ is 5-chloro, $R^2$ is ethyl and the radical $R^3$ for each compound corresponds to one line of Table A Table 382
Compounds of the formula I.6a where $(X)_m$ is 5-chloro, $R^2$ is n-propyl and the radical $R^3$ for each compound corresponds to one line of Table A Table 383
Compounds of the formula I.6a where $(X)_m$ is 5-chloro, $R^2$ is isopropyl and the radical $R^3$ for each compound corresponds to one line of Table A Table 384
Compounds of the formula I6a where $(X)_m$ is 5-chloro, $R^2$ is cyano and the radical $R^3$ for each compound corresponds to one line of Table A Table 385
Compounds of the formula I.6a where $(X)_m$ is 3-bromo, $R^2$ is hydrogen and the radical $R^3$ for each compound corresponds to one line of Table A Table 386
Compounds of the formula I.6a where $(X)_m$ is 3-bromo, $R^2$ is methyl and the radical $R^3$ for each compound corresponds to one line of Table A Table 387
Compounds of the formula I.6a where $(X)_m$ is 3-bromo, $R^2$ is ethyl and the radical $R^3$ for each compound corresponds to one line of Table A Table 388
Compounds of the formula I.6a where $(X)_m$ is 3-bromo, $R^2$ is n-propyl and the radical $R^3$ for each compound corresponds to one line of Table A Table 389
Compounds of the formula I.6a where $(X)_m$ is 3-bromo, $R^2$ is isopropyl and the radical $R^3$ for each compound corresponds to one line of Table A Table 390
Compounds of the formula I.6a where $(X)_m$ is 3-bromo, $R^2$ is cyano and the radical $R^3$ for each compound corresponds to one line of Table A Table 391
Compounds of the formula I.6a where $(X)_m$ is 4-bromo, $R^2$ is hydrogen and the radical $R^3$ for each compound corresponds to one line of Table A Table 392
Compounds of the formula I.6a where $(X)_m$ is 4-bromo, $R^2$ is methyl and the radical $R^3$ for each compound corresponds to one line of Table A Table 393
Compounds of the formula I.6a where $(X)_m$ is 4-bromo, $R^2$ is ethyl and the radical $R^3$ for each compound corresponds to one line of Table A Table 394
Compounds of the formula I.6a where $(X)_m$ is 4-bromo, $R^2$ is n-propyl and the radical $R^3$ for each compound corresponds to one line of Table A Table 395
Compounds of the formula I.6a where $(X)_m$ is 4-bromo, $R^2$ is isopropyl and the radical $R^3$ for each compound corresponds to one line of Table A Table 396
Compounds of the formula I.6a where $(X)_m$ is 4-bromo, $R^2$ is cyano and the radical $R^3$ for each compound corresponds to one line of Table A Table 397
Compounds of the formula I.6a where $(X)_m$ is 5-bromo, $R^2$ is hydrogen and the radical $R^3$ for each compound corresponds to one line of Table A Table 398
Compounds of the formula I.6a where $(X)_m$ is 5-bromo, $R^2$ is methyl and the radical $R^3$ for each compound corresponds to one line of Table A Table 399
Compounds of the formula I.6a where $(X)_m$ is 5-bromo, $R^2$ is ethyl and the radical $R^3$ for each compound corresponds to one line of Table A Table 400
Compounds of the formula I.6a where $(X)_m$ is 5-bromo, $R^2$ is n-propyl and the radical $R^3$ for each compound corresponds to one line of Table A Table 401
Compounds of the formula I.6a where $(X)_m$ is 5-bromo, $R^2$ is isopropyl and the radical $R^3$ for each compound corresponds to one line of Table A Table 402
Compounds of the formula I.6a where $(X)_m$ is 5-bromo, $R^2$ is cyano and the radical $R^3$ for each compound corresponds to one line of Table A Table 403
Compounds of the formula I.6a where $(X)_m$ is 3-nitro, $R^2$ is hydrogen and the radical $R^3$ for each compound corresponds to one line of Table A Table 404
Compounds of the formula I.6a where $(X)_m$ is 3-nitro, $R^2$ is methyl and the radical $R^3$ for each compound corresponds to one line of Table A Table 405
Compounds of the formula I.6a where $(X)_m$ is 3-nitro, $R^2$ is ethyl and the radical $R^3$ for each compound corresponds to one line of Table A Table 406
Compounds of the formula I.6a where $(X)_m$ is 3-nitro, $R^2$ is n-propyl and the radical $R^3$ for each compound corresponds to one line of Table A Table 407
Compounds of the formula I.6a where $(X)_m$ is 3-nitro, $R^2$ is isopropyl and the radical $R^3$ for each compound corresponds to one line of Table A Table 408
Compounds of the formula I.6a where $(X)_m$ is 3-nitro, $R^2$ is cyano and the radical $R^3$ for each compound corresponds to one line of Table A Table 409
Compounds of the formula I.5a where $(X)_m$ is 4-nitro, $R^2$ is hydrogen and the radical $R^3$ for each compound corresponds to one line of Table A Table 410
Compounds of the formula I.6a where $(X)_m$ is 4-nitro, $R^2$ is methyl and the radical $R^3$ for each compound corresponds to one line of Table A Table 411
Compounds of the formula I.6a where $(X)_m$ is 4-nitro, $R^2$ is ethyl and the radical $R^3$ for each compound corresponds to one line of Table A Table 412
Compounds of the formula I.6a where $(X)_m$ is 4-nitro, $R^2$ is n-propyl and the radical $R^3$ for each compound corresponds to one line of Table A Table 413
Compounds of the formula I.6a where $(X)_m$ is 4-nitro, $R^2$ is isopropyl and the radical $R^3$ for each compound corresponds to one line of Table A Table 414
Compounds of the formula I.6a where $(X)_m$ is 4-nitro, $R^2$ is cyano and the radical $R^3$ for each compound corresponds to one line of Table A Table 415
Compounds of the formula I.6a where $(X)_m$ is 5-nitro, $R^2$ is hydrogen and the radical $R^3$ for each compound corresponds to one line of Table A Table 416
Compounds of the formula I.6a where $(X)_m$ is 5-nitro, $R^2$ is methyl and the radical $R^3$ for each compound corresponds to one line of Table A Table 417
Compounds of the formula I.6a where $(X)_m$ is 5-nitro, $R^2$ is ethyl and the radical $R^3$ for each compound corresponds to one line of Table A Table 418
Compounds of the formula I.6a where $(X)_m$ is 5-nitro, $R^2$ is n-propyl and the radical $R^3$ for each compound corresponds to one line of Table A Table 419
Compounds of the formula I.6a where $(X)_m$ is 5-nitro, $R^2$ is isopropyl and the radical $R^3$ for each compound corresponds to one line of Table A Table 420
Compounds of the formula I.6a where $(X)_m$ is 5-nitro, $R^2$ is cyano and the radical $R^3$ for each compound corresponds to one line of Table A

TABLE A

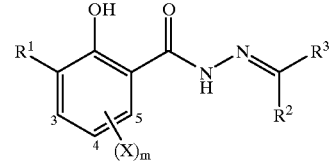

I

| No. | $R^3$ | $R^b$ |
|---|---|---|
| A-1 | c-$C_6H_{11}$ | — |
| A-2 | c-$C_6H_{10}$ | 2-Cl |
| A-3 | c-$C_6H_{10}$ | 3-Cl |
| A-4 | c-$C_6H_{10}$ | 4-Cl |
| A-5 | c-$C_6H_{10}$ | 2-Br |
| A-6 | c-$C_6H_{10}$ | 3-Br |
| A-7 | c-$C_6H_{10}$ | 4-Br |
| A-8 | c-$C_6H_{10}$ | 2-$NO_2$ |
| A-9 | c-$C_6H_{10}$ | 3-$NO_2$ |
| A-10 | c-$C_6H_{10}$ | 4-$NO_2$ |
| A-11 | c-$C_6H_{10}$ | 4-$NO_2$ |

TABLE A-continued

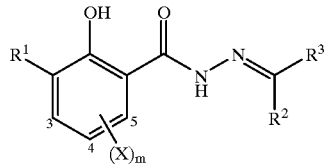

| No. | $R^3$ | $R^b$ |
|---|---|---|
| A-11 | c-$C_6H_{10}$ | 2-CN |
| A-12 | c-$C_6H_{10}$ | 3-CN |
| A-13 | c-$C_6H_{10}$ | 4-CN |
| A-14 | c-$C_6H_{10}$ | 2-$CH_3$ |
| A-15 | c-$C_6H_{10}$ | 3-$CH_3$ |
| A-16 | c-$C_6H_{10}$ | 4-$CH_3$ |
| A-17 | c-$C_6H_9$ | 2,4-$(Cl)_2$ |
| A-18 | c-$C_6H_9$ | 2,4-$(Br)_2$ |
| A-19 | c-$C_6H_9$ | 2,4-$(NO_2)_2$ |
| A-20 | c-$C_6H_9$ | 2,4-$(CH_3)_2$ |
| A-21 | c-$C_6H_{10}$ | 4-$CH_2CH_3$ |
| A-22 | c-$C_6H_{10}$ | 4-$CH_2CH_2CH_3$ |
| A-23 | c-$C_6H_{10}$ | 4-$CH(CH_3)_2$ |
| A-24 | c-$C_6H_{10}$ | 4-$CH_2CH_2CH_2CH_3$ |
| A-25 | c-$C_6H_{10}$ | 4-$CH_2CH(CH_3)_2$ |
| A-26 | $C_6H_5$ | — |
| A-27 | $C_6H_4$ | 2-Cl |
| A-28 | $C_6H_4$ | 3-Cl |
| A-29 | $C_6H_4$ | 4-Cl |
| A-30 | $C_6H_4$ | 2-Br |
| A-31 | $C_6H_4$ | 3-Br |
| A-32 | $C_6H_4$ | 4-Br |
| A-33 | $C_6H_4$ | 2-$NO_2$ |
| A-34 | $C_6H_4$ | 3-$NO_2$ |
| A-35 | $C_6H_4$ | 4-$NO_2$ |
| A-36 | $C_6H_4$ | 2-CN |
| A-37 | $C_6H_4$ | 3-CN |
| A-38 | $C_6H_4$ | 4-CN |
| A-39 | $C_6H_4$ | 2-$CH_3$ |
| A-40 | $C_6H_4$ | 3-$CH_3$ |
| A-41 | $C_6H_4$ | 4-$CH_3$ |
| A-42 | $C_6H_4$ | 4-$CH_2CH_3$ |
| A-43 | $C_6H_4$ | 4-$CH_2CH_2CH_3$ |
| A-44 | $C_6H_4$ | 4-$CH(CH_3)_2$ |
| A-45 | $C_6H_4$ | 4-$CH_2CH_2CH_2CH_3$ |
| A-46 | $C_6H_4$ | 4-$CH_2CH(CH_3)_2$ |
| A-47 | $C_6H_4$ | 4-$C(CH_3)_3$ |
| A-48 | $C_6H_4$ | 4-$C_6H_5$ |
| A-49 | $C_6H_4$ | 4-(2-Cl)—$C_6H_4$ |
| A-50 | $C_6H_4$ | 4-(3-Cl)—$C_6H_4$ |
| A-51 | $C_6H_4$ | 4-(4-Cl)—$C_6H_4$ |
| A-52 | $C_6H_4$ | 4-(2-Br)—$C_6H_4$ |
| A-53 | $C_6H_4$ | 4-(3-Br)—$C_6H_4$ |
| A-54 | $C_6H_4$ | 4-(4-Br)—$C_6H_4$ |
| A-55 | $C_6H_4$ | 4-(2-$NO_2$)—$C_6H_4$ |
| A-56 | $C_6H_4$ | 4-(3-$NO_2$)—$C_6H_4$ |
| A-57 | $C_6H_4$ | 4-(4-$NO_2$)—$C_6H_4$ |
| A-58 | $C_6H_4$ | 4-(2-CN)—$C_6H_4$ |
| A-59 | $C_6H_4$ | 4-(3-CN)—$C_6H_4$ |
| A-60 | $C_6H_4$ | 4-(4-CN)—$C_6H_4$ |
| A-61 | $C_6H_4$ | 4-(2-$CH_3$)—$C_6H_4$ |
| A-62 | $C_6H_4$ | 4-(3-$CH_3$)—$C_6H_4$ |
| A-63 | $C_6H_4$ | 4-(4-$CH_3$)—$C_6H_4$ |
| A-64 | $C_6H_4$ | 4-(2,4-$Cl_2$)—$C_6H_3$ |
| A-65 | $C_6H_4$ | 4-(2,4-$Br_2$)—$C_6H_3$ |
| A-66 | $C_6H_4$ | 4-[2,4-$(NO_2)_2$]—$C_6H_3$ |
| A-67 | $C_6H_4$ | 4-[2,4-$(CH_3)_2$]—$C_6H_3$ |

The compounds I are suitable as fungicides. They are distinguished by an outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar-acting and soil-acting fungicides. They are especially important for controlling a multiplicity of fungi on a series of crop plants such as wheat, rye, barley, oats, rice, maize, grass, bananas, cotton, soya, coffee, sugar cane, grapevines, fruit plants, ornamentals and vegetable plants such as cucumbers, beans, tomatoes, potatoes and cucurbits, and on the seeds of these plants.

Specifically, they are suitable for controlling the following plant diseases:

Alternaria species on vegetable and fruit,
Botrytis cinerea (gray mold) on strawberries, vegetables, ornamentals and grapevines,
Cercospora arachidicola on peanuts,
Erysiphe cichoracearum and Sphaerotheca fuliginea on cucurbits,
Erysiphe graminis (powdery mildew) on cereals,
Fusarium and Verticillium species on a variety of plants,
Helminthosporium species on cereals,
Mycosphaerella species on bananas and peanuts,
Phytophthora infestans on potatoes and tomatoes,
Plasmopara viticola on grapevines,
Podosphaera leucotricha on apples,
Pseudocercosporella herpotrichoides on wheat and barley,
Pseudoperonospora species on hops and cucumbers,
Puccinia species on cereals,
Pyricularia oryzae on rice,
Rhizoctonia species on cotton, rice and lawns,
Septoria nodorum on wheat,
Uncinula necator on grapevines,
Ustilago species on cereals and sugar cane, and
Venturia species (scab) on apples and pears.

Moreover, the compounds I are suitable for controlling harmful fungi such as Paecilomyces variotii in the protection of materials (for example wood, paper, paint dispersions, fibers and fabrics) and in the protection of stored products.

The compounds I are applied by treating the fungi, or the plants, seeds, materials to be protected against fungal infection, or the soil, with a fungicidally effective amount of the active ingredients. Application can be effected both before and after infection of the materials, plants or seeds by the fungi.

In general, the fungicidal compositions comprise from 0.1 to 95, preferably from 0.5 to 90, % by weight of active ingredient.

When used in crop protection, the application rates are from 0.01 to 2.0 kg of active ingredient per ha, depending on the nature of the desired effect.

In the treatment of seed, amounts of active ingredient of from 0.001 to 0.1 g, preferably 0.01 to 0.05 g, are generally required per kilogram of seed.

When used in the protection of materials or stored products, the application rate of active ingredient depends on the nature of the field of application and on the desired effect. Conventionally used application rates in the protection of materials are, for example, from 0.001 g to 2 kg, preferably 0.005 g to 1 kg, of active ingredient per cubic meter of material treated.

The compounds I can be converted into the customary formulations, e.g. solutions, emulsions, suspensions, dusts, powders, pastes and granules. The use form depends on the particular purpose; it is intended to ensure in each case a fine and uniform distribution of the compound according to the invention.

The formulations are prepared in a known manner, e.g. by extending the active ingredient with solvents and/or carriers, if desired using emulsifiers and dispersants, it also being possible to use other organic solvents as cosolvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly dispersed silica, silicates); emulsifiers such as nonionic and anionic emulsifiers (e.g., polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, napthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and napthalene derivatives with formaldehyde, condensates of napthalene or of naphthalenesulfonic acid with phenol and formaldehyde, polyoxyethylene octylphenyl ether, ethoxylated isooctyl phenol, octyl phenol, nonyl phenol, alkyl phenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin sulfite waste liquors and methyl cellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for spreading and dusts can be prepared by mixing or concomitantly grinding the active substances together with a solid carrier.

Granules, e.g. coated granules, impregnated granules and homogeneous granules, can be prepared by binding the active ingredients to solid carriers. Examples of solid carriers are mineral earths, such as silica gels, silicic acids, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (active ingredient content 9% by weight)

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60% by weight of pulverulent silica gel, and the mixture is ground in a hammer mill. Finely distributing the mixture in 20,000 parts by weight of water gives a spray mixture comprising 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; they are intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentration in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, or herbicides, fungicides, other pesticides or bactericides may be added to the active ingredients, if appropriate just immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broadened fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)-benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl) formamide, 1-(3,4-dichloroanilino)-1-formylamino-2,2,2-trichloroethane;

amines such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3- (p-tert-butylphenyl)-2-methylpropyl]-piperidine;

azoles such as 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1- (1H-1,2,4-triazol-1-yl) -2-butanol, (2RS,3RS)-1-[3-(2-chlorophenyl)-2-(4-fluorophenyl)oxiran-2-yl-methyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxylphenyl}-3-methoxyacrylate, N-methyl-E-methoxy-imino-[α-(2-phenoxyphenyl)]acetamide, N-methyl E-methoxyimino-(α-(2,5-dimethylphenoxy)-o-tolyl]acetamide;

anilinopyrimidines such as N-(4,6-dimethylpyrimidin-2-yl) aniline, N-[4-methyl-6-(1-propynyl)pyrimidin-2-yl] aniline, N-[4-methyl-6-cyclopropylpyrimidin-2-yl] aniline;

phenylpyrroles such as 4-(2,2-difluoro-1,3-benzodioxol-4-yl)pyrrole-3-carbonitrile;

cinnanamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α- (1H-1,2,4-triazolyl-1-methyl)benzhydryl alcohol, N-(3-chloro-2,6- dinitro-4-trifluoromethylphenyl)-5-trifluoromethyl-3-chloro-2-aminopyridin, 1-((bis-(4-fluorophenyl)methylsilyl)methyl)-1H-1,2,4-triazole.

SYNTHESIS EXAMPLES

The protocols shown in the synthesis examples herebelow were used for obtaining further compounds I, except that the starting compounds were changed as appropriate. The resulting compounds are listed in the tables which follow together with physical data.

Example 1

Preparation of 2-hydroxy-3-nitrobenzhydrazide

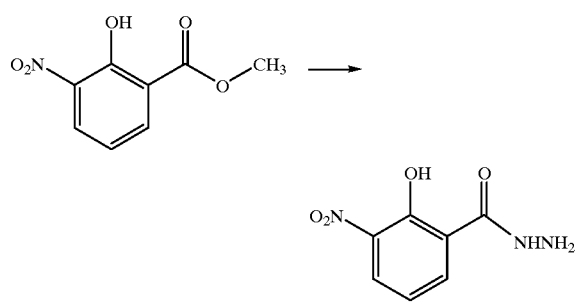

40 ml of hydrazine hydrate were added to a solution of 30 g (0.15 mol) of methyl 3-nitrosalicylate in 200 ml of anhydrous tetrahydrofuran (THF). After dilution with THF, the resulting suspension was stirrable; it was refluxed for approximately 18 hours. After cooling, the batch was poured onto ice. The aqueous solution was rendered neutral by adding NaOH solution. The crystals which precipitated were filtered off and washed with water. After drying, 27 g (90%) of the title compound were obtained.

Example 2

Preparation of 3-nitrosalicylic (1-phenylethylidene) hydrazide

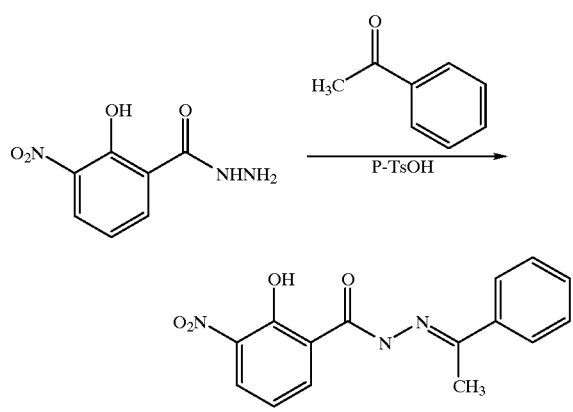

A solution of 1.0 g (5 mmol) of 3-nitrosalicylohydrazide in 50 ml of anhydrous ethanol were treated with 0.6 g (5 mmol) of acetophenone and with a catalytic amount of p-toluenesulfonic acid. After the mixture had been stirred for 14 hours at approximately 20 to 25° C. and the solvent had been distilled off, 1.4 g of the title compound (90% of theory) were obtained as colorless crystals of m.p.: 163–168° C.

TABLE I

I

| No. | $R^1$ | $(X)_m$ | $R^2$ | $R^3$ | M.p. [° C.] |
|---|---|---|---|---|---|
| I-1 | $NO_2$ | H | $CH_3$ | $C_6H_5$ | 163–168 |
| I-2 | $NO_2$ | H | H | $C_6H_5$ | 193–199 |
| I-3 | $NO_2$ | H | $CH_3$ | $4\text{-}CH_3\text{—}C_6H_4$ | 149–154 |
| I-4 | $NO_2$ | H | H | $4\text{-}CH_3\text{—}C_6H_4$ | 160–166 |
| I-5 | $NO_2$ | H | $CH_3$ | $4\text{-}Cl\text{—}C_6H_4$ | 194–197 |
| I-6 | $NO_2$ | H | H | $4\text{-}Cl\text{—}C_6H_4$ | 192–196 |
| I-7 | $NO_2$ | H | $CH_3$ | $4\text{-}Br\text{—}C_6H_4$ | 194–197 |
| I-8 | $NO_2$ | H | H | $4\text{-}Br\text{—}C_6H_4$ | 174–178 |
| I-9 | $NO_2$ | H | $CH_3$ | $4\text{-}NO_2\text{—}C_6H_4$ | 204–208 |
| I-10 | $NO_2$ | H | H | $4\text{-}NO_2\text{—}C_6H_4$ | 240–244 |
| I-11 | $NO_2$ | H | $CH_3$ | $4\text{-}CN\text{—}C_6H_4$ | 218–222 |
| I-12 | $NO_2$ | H | H | $4\text{-}CN\text{—}C_6H_4$ | 220–223 |
| I-13 | $NO_2$ | H | $CH_3$ | $4\text{-}OCH_3\text{—}C_6H_4$ | 146–150 |
| I-14 | $NO_2$ | H | H | $4\text{-}OCH_3\text{—}C_6H_4$ | 167–172 |
| I-15 | $NO_2$ | H | $CH_3$ | $2,4\text{-}(OCH_3)_2\text{—}C_6H_4$ | 245–248 |
| I-16 | $NO_2$ | H | H | $2,4\text{-}(OCH_3)_2\text{—}C_6H_4$ | 207–210 |
| I-17 | $NO_2$ | H | $CH_3$ | $2,4\text{-}Cl_2\text{—}C_6H_4$ | 110–114 |
| I-18 | $NO_2$ | H | H | $2,4\text{-}Cl_2\text{—}C_6H_4$ | 219–223 |
| I-19 | $NO_2$ | H | $CH_3$ | $4\text{-}C_6H_5\text{—}C_6H_4$ | 209–212 |
| I-20 | $NO_2$ | H | H | $4\text{-}C_6H_5\text{—}C_6H_4$ | 189–195 |

Examples of the action against harmful fungi

The fungicidal action of the compounds of the general formula I was demonstrated by the following experiments:

The active ingredients, separately or together, were formulated as a 10% emulsion in a mixture of 70% by weight of cyclohexanone, 20% by weight of Nekanil® LN (Lutensol® AP6, wetter with emulsifier and dispersant action based on ethoxylated alkylphenols) and 10% by weight of Wettol® EM (nonionic emulsifer based on ethoxylated castor oil) and the formulations were diluted with water to give the desired concentration.

Use example—activity against Botrytis cinerea on capsicum leaves

After 4–5 leaves had developed properly, capsicum seedlings cv. "Neusiedler Ideal Elite" were sprayed to runoff point with an aqueous preparation of active ingredient made with a stock solution of 10% of active ingredient, 63% of cyclohexanone and 27% of emulsifier. Next day, the treated plants were inoculated with a spore suspension of Botrytis cinerea which contained $1.7 \times 10^6$ spores/ml in a 2% strength aqueous Biomite solution. The test plants were subsequently placed into a controlled-environment cabinet at 22–24° C. and high atmospheric humidity. After 5 days, it was possible to determine the extent of fungal infection on the leaves visually in %.

In this test, the disease level of the plants treated with a 250 ppm formulation of the active ingredient I-1, I-3 and I-6 was not more than 15%, while it was 90% in the case of the untreated plants.

We claim:

1. A salicylohydrazide compound of formula ID $$\text{(I)}$$

$$\text{(ID)}$$

in which the index and the substituents have the following meanings:
  $R^1$ is $NO_2$, $NH_2$ or $NH-CO-A$;
    A is hydrogen, $C_1-C_4$-alkyl, $C_1-C_4$-alkoxy, $NH_2$, $NHCH_3$ or $N(CH_3)_2$;
  $R^2$ is hydrogen, cyano, $C_1-C_6$-alkyl, $C_2-C_6$-alkenyl, $C_2-C_6$-alkynyl, $C_1-C_6$-haloalkyl, $C_1-C_6$-alkoxy or $C_1-C_6$-alkylthio;
    it being possible for the hydrocarbon radicals to be unsubstituted or to be partially or fully halogenated or to have 1 to 3 groups $R^a$
      $R^a$ is halogen, cyano, nitro, hydroxyl, $C_1-C_6$-alkyl, $C_1-C_6$-haloalkyl, $C_1-C_6$-alkylcarbonyl, $C_3-C_6$-cycloalkyl, $C_1-C_6$-alkoxy, $C_1-C_6$-haloalkoxy, $C_1-C_6$-alkoxycarbonyl, $C_1-C_6$-alkylthio, $C_1-C_6$-alkylamino, di-$C_1-C_6$-alkylamino, $C_2-C_6$-alkenyl, $C_3-C_6$-alkenyloxy, $C_3-C_6$-alkynyloxy or $C_1-C_4$-alkylenedioxy which can be halogenated,
  $R^3$ is phenyl, naphthyl, $C_3-C_{10}$-cycloalkyl, the ring systems being unsubstituted or substituted by one to three radicals $R^b$:
    $R^b$ is cyano, nitro, amino, aminocarbonyl, aminothiocarbonyl, halogen, hydroxyl, $C_1-C_6$-alkyl, $C_1-C_6$-haloalkyl, $C_1-C_6$-alkylcarbonyl, $C_1-C_6$-alkylsulfonyl, $C_1-C_6$-alkylsulfoxyl, $C_3-C_6$-cycloalkyl, $C_1-C_6$-alkoxy, $C_1-C_6$-haloalkoxy, $C_1-C_6$-alkyloxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, phenyl, phenoxy, benzyl, benzyloxy, 5- or 6-membered heterocyclyl, 5- or 6-membered hetaryl, 5- or 6-membered hetaryloxy, $C(=NOR^\alpha)-OR^\beta$ or $OC(R^\alpha)_2-C(R^\beta)=NOR^\beta$,
      the cyclic radicals, in turn, being unsubstituted or substituted by one to three radicals $R^c$:
        $R^c$ is cyano, nitro, halogen, hydroxyl, amino, aminocarbonyl, aminothiocarbonyl, $C_1-C_6$-alkyl, $C_1-C_6$-haloalkyl, $C_1-C_6$-alkylsulfonyl, $C_1-C_6$-alkylsulfoxyl, $C_3-C_6$-cycloalkyl, $C_1-C_6$-alkoxy, $C_1-C_6$-haloalkoxy, $C_1-C_6$-alkoxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, $C_3-C_6$-cycloalkyl, $C_3-C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or $C(=NOR^\alpha)-OR^\beta$;
          $R^\alpha$, $R^\beta$ are hydrogen or $C_1-C_6$-alkyl.

2. The compound of formula ID defined in claim 1 where $R^1$ is $NH-CO-A$.

3. The compound of formula ID defined in claim 1 where
  A is hydrogen, $C_1-C_4$-alkoxy, $NHCH_3$ or $N(CH_3)_2$:
  $R^2$ is CN or $C_1-C_6$-alkyl;
  $R^3$ is phenyl which is unsubstituted or substituted by one to three radicals $R^b$.

4. A process for the preparation of the compound of formula ID defined in claim 1 by reacting a hydrazide of formula II'

$$\text{II'}$$

with a carbonyl compound of formula III $$\text{III}$$

to give a compound of formula IA'

$$\text{IA'}$$

and, to prepare the compound of formula ID where $R^1$ is $NH_2$ or $NH-CO-A$, hydrogenating the compound of formula IA' to give an aminophenol compound of formula IB', $$\text{IB'}$$

and, to prepare the compound of formula ID where $R^1$ is $NH-CO-H$, formylating the compound of formula IB' to give a compound of formula I.1'

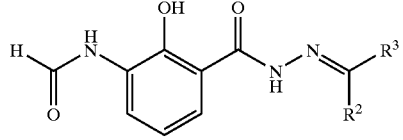

or, to prepare the compound of formula ID where $R^1$ is NH—CO—NH$_2$, reacting the compound of formula IB' with an alkali metal isocyanate or an alkaline earth metal isocyanate to give a compound of formula I.2',

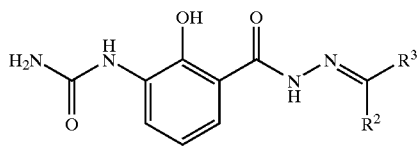

or, to prepare the compound of formula ID where $R^1$ is NH—CO—NHCH$_3$, reacting the comporund of formula IB' with methyl isocyanate to give a compound of formula I.3',

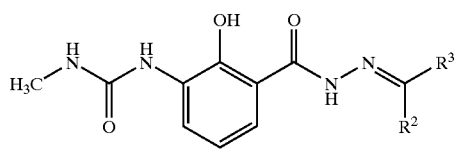

or, to prepare the compound of formula ID where $R^1$ is NH—CO—N(CH$_3$)$_2$, reacting the compound of formula IB' with phosgene and dimethylamine to give a compound of formula I.4',

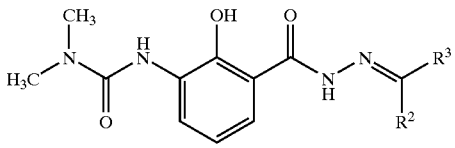

or, to prepare the compound of formula ID in which $R^1$ is NH—CO—OCH$_3$, reacting the compound of formula IB' with carbon monoxide and methanol with transition-metal catalysis to give a compound of formula I.5'

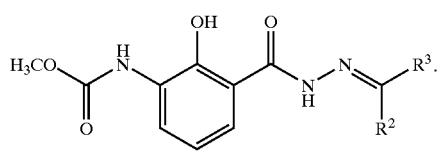

5. A composition which is suitable for controlling phytopathogenic harmful fungi, comprising a solid or liquid carrier and the compound of formula ID defined in claim 1.

6. A method of controlling phytopathogenic harmful fungi, which comprises treating the fungi, or materials, plants, soil or seed to be protected from fungal attack, with an effective amount of the compound of formula ID defined in claim 1.

* * * * *